US007425531B2

(12) United States Patent
Lanctot et al.

(10) Patent No.: US 7,425,531 B2
(45) Date of Patent: Sep. 16, 2008

(54) BONE POLYPEPTIDE-1

(75) Inventors: Christian Lanctot, Mont St-Hilaire (CA); Patrick Salois, Montreal (CA); Pierre Moffatt, Lachine (CA)

(73) Assignee: Enobia Pharma Inc., Montreal, Quebec (CA)

( * ) Notice: Subject to any disclaimer, the term of this patent is extended or adjusted under 35 U.S.C. 154(b) by 0 days.

(21) Appl. No.: 10/499,762

(22) PCT Filed: Dec. 20, 2002

(86) PCT No.: PCT/IB02/05778

§ 371 (c)(1),
(2), (4) Date: Aug. 4, 2004

(87) PCT Pub. No.: WO03/054005

PCT Pub. Date: Jul. 3, 2003

(65) Prior Publication Data

US 2005/0143562 A1 Jun. 30, 2005

Related U.S. Application Data

(60) Provisional application No. 60/341,224, filed on Dec. 20, 2001.

(51) Int. Cl.
*A61K 38/00* (2006.01)
*A61K 38/17* (2006.01)
(52) U.S. Cl. .............................. 514/2; 514/12; 530/300; 530/350; 435/6; 435/69.1; 435/320.1; 536/23.5
(58) Field of Classification Search .................... 514/2, 514/12; 530/350, 300; 435/6, 69.1, 320.1; 536/23.5
See application file for complete search history.

(56) References Cited

U.S. PATENT DOCUMENTS

2007/0042374 A1 2/2007 Shimomura et al.
2007/0049521 A1 3/2007 Lanctot et al.

OTHER PUBLICATIONS

Andréa Frota Ruchon et al., "Development Expression and Tissue Distribution of Phex Protein : Effect of the Hyp Mutation and Relationship to Bone Markers", Journal of Bone and Mineral Research, vol. 14, No. 8, 2000, pp. 1440-1450.
Steven Henikoff et al., "Automated Assembly of Protein Blocks for Database Searching", Nucleic Acids Research, vol. 19, No. 23, 1991, pp. 6565-6572.
Thomas P. Hopp et al., "Prediction of Protein Antigenic Determinants From Amino Acid Sequences", Proc. Natl. Acad. Sci. USA, vol. 78, No. 6, Jun. 1981, pp. 3824-3828.
F. Francis et al., "A Gene (PEX) With Homologies to Endopeptidases is Mutated in Patients With X-Linked Hypophosphatemic Rickets", Nature Genetics, vol. 11, Oct. 1995, pp. 130-136.

T. Inagami et al., "Biochemical Studies of Rat Atrial Natriuretic Factor", Clin. and Exper.—Theory and Practice, A7(5 & 6), 1985, pp. 851-866.
R. Kumar, "Tumor-Induced Osteomalacia and the Regulation of Phosphate Homeostasis", Bone, vol. 27, No. 3, Sep. 2000, pp. 333-338.
Vishwanath R. Lingappa et al., "Cell-Free Synthesis and Segregation of $\beta_2$ -Microglobulin", Proc. Natl, Acad. Sci. USA, vol. 76, No. 8, Aug. 1979, pp. 3651-3655.
Nathalle Louis et al., "Cloning and Sequencing of the Cellular—Viral Junctions From the Human Adenovirus Type 5 Transformed 293 Cell Line", Virology 233, Article No. VY978597, 1997, pp. 423-429.
Hiroshi Mayahara et al., "In Vivo Stimulation of Endosteal Bone Formation by Basic Fibroblast Growth Factor in Rats", Growth Factors, vol. 9, 1993, pp. 73-80.
Stavros C. Manolagas, "Birth and Death of Bone Cells: Basic Regulatory Mechanisms and Implications for the Pathogenesis and Treatment of Osteoporosis", Endocrine Reviews 21(2), 2000, pp. 115-137.
Kazuo Maruyama et al., "Oligo-Capping: A Simple Method to Replace the Cap Structure of Eukaryotic MRNAS With Oligoribonucleotides", Gene, 138, 1994, pp. 171,174.
Nicola C. Partridge et al., "Morphological and Biochemical Characterization of Four Clonal Osteogenic Sarcoma Cell Lines of Rat Origin", Cancer Research, 43, Sep. 1983, pp. 4308-4314.
William R. Pearson et al., "Improved Tools for Biological Sequence Comparison", Proc. Natl. Acad. Sci. USA, vol. 85, Apr. 1988, pp. 2444-2448.
Thierry Ragot et al., "Adenoviral Gene Delivery", chap.11 In: "Methods in Cell Biology", vol. 52, 1998, pp. 229-260.
Andréa Frota Ruchion et al., "PEX MRNA is Localized in Developing Mouse Osteoblasts and Odontoblasts", J. of Histochemistry & Cytochemistry, vol. 46(4), 1998, pp. 459-468.
R. G. G. Russell et al., "Biosposphonates: From the Laboratory to the Clinic and Back Again", Bone, vol. 25, No. 1, Jul. 1999, pp. 97-106.
T. F. Smith et al., "Identification of Common Molecular Subsequences", J. Mol. Biol., 147, 1981, pp. 195-197.
Theodore J. Tsomides et al., "Stoichiometric Labeling of Peptides by Iodination on Tyrosyl or Histidyl Residues", Analytical Biochemistry, 210, 1993, pp. 129-135.
Wei Yan et al., "Corin, A Mosaic Transmembrane Serine Protease Encoded by a Novel CDNA From Human Heart", J. Biol. Chem., vol. 274, No. 21, May 21, 1999, pp. 14926-14935.
Wei Yan et al., "Corin, A Transmembrane Cardiac Serine Protease, Acts as a Pro-Atrial Natriuretic Peptide-Converting Enzyme", PNAS, vol. 97, No. 15, Jul. 18, 2000, pp. 8525-8529.
Patricia Ducy et al., "Leptin Inhibits Bone Formation Through a Hypothalamic Relay : A Central Control of Bone Mass", Cell, vol. 100, Jan. 21, 2000, pp. 197-207.

(Continued)

*Primary Examiner*—Chih-Min Kam
(74) *Attorney, Agent, or Firm*—Brian R. Dorn; Merchant & Gould P.C.

(57) ABSTRACT

The present invention relates to a bone polypeptide, particularly bone polypeptide-1 and nucleic acid molecules encoding the same. The present invention provides the human primary sequence of bone polypeptide-1 as well as sequences of vertebrate homologs. The invention also provides cell lines engineered to express the cDNA, antibodies to detect its translation products, and recombinant adenoviruses to deliver an expressible cDNA into a host. Bone polypeptide-1 can be utilized to treat diseases affecting renal and bone functions.

30 Claims, 15 Drawing Sheets

OTHER PUBLICATIONS

Patricia Ducy "CBFA1 : A Molecular Switch in Osteoblast Biology", Developmental Dynamics, 219, 2000, pp. 461-471.

Mariyln Kozak, "Point Mutations Define a Sequence Flanking the Aug Initiator Codon That Modulates Translation by Eukaryotic Ribosomes", Cell, vol. 44, Jan. 31, 1986, pp. 283-292.

Stephen F. Altschul, "A Protein Alignment Scoring System Sensitive at All Evolutionary Distances", J. Mol. Evol., 36, 1993, pp. 290-300.

Gillian, M. Olins, "A Linear Analog of Atrial Natriuretic Peptide (ANP) Discriminates Guanylate Cyclase-Coupled ANP Receptors From Non-Coupled Receptors", The Journal of Biological Chemistry, vol. 263, No. 22, Aug. 5, 1988, pp. 10989-10993.

Robert M. Neer, "Effect of Parathyroid Hormone (1-34) on Fractures and Bone Mineral Density in Postmenopausal Women With Osteoporosis", N. Engl. J. Med., vol. 344, No. 19, May 10, 2001, pp. 1434-1441.

Saul B. Needleman et al., "A General Method Applicable to the Search for Similarities in the Amino Acid Sequence of Two Proteins", J. Mol. Biol., 48, 1970, pp. 443-453.

David G. Wilkinson, "Detection of Messenger RNA by in Situ Hybridization to Tissue Sections and Whole Mounts", Methods in Enzymology, vol. 225, 1993, pp. 361-372.

R. H. Unger, "Leptin Physilology: A Second Look", Regulatory Peptides, 92, 2000, pp. 87-95.

Samuel Karlin et al., "Methods for Assessing the Statistical Significance of Molecular Sequence Features by Using General Scoring Schemes", Proc. Natl. Acad. Sci. USA, vol. 87, Mar. 1990, pp. 2264-2268.

Samuel Karlin et al., "Applications and Statistics for Multiple High-Scoring Segments in Molecular Sequences", Proc. Natl. Acad. Sci. USA, vol. 90, Jun. 1993, pp. 5873-5877.

Eugene W. Myers, "An Overview of Sequence Comparison Algorithms in Molecular Biology", Technical Report, 29, Department of Computer Science, University of Arizona, 1991, 42 p.

Bleakman, A. et al., "Sequential processing reactions in the formation of hormone amides," Eur. J. Biochem., vol. 167, No. 1, pp. 161-165 (Aug. 17, 1987) (1 page abstract).

Office Action of Jun. 27, 2007 for U.S. Appl. No. 11/210,631 (U.S. Pat. Appl. Pub. No. 2007/0049521).

Elisabeth M. Aarden et al., "Function of Osteocytes in Bone", Journal of Cellular Biochemistry, 55, 1994, pp. 287-299.

Cedo M. Bagi et al., "Systemic Administration of RHIGF-I or RHIGF-I/IGFBP-3 Increases Cortical Bone and Lean Body Mass in Ovariectomized Rats", Bone, vol. 16, No. 4, 1995, pp. 263S-269S.

Roland Baron, "Anatomy and Ultrastructure of Bone", Chap. 1 in: "Primer on the Metabolic Bone Diseases and Disorders of Mineral Metabolism", pp. 3-10, (2006).

Roger S. Birnbaum et al. "Ontogeny of Peptidyglycine Alpha-Amidating Monooxygenase Activity in Rapidly Mineralizing Bone From Neonatal Mouse", Endocrinology, vol. 124, No. 6, 1989, pp. 3134-3136.

Piotr Chomczynski et al., "Single-Step Method of RNA Isolation by Acid Guanidinium Thiocyanate-Phenol-Chloroform Extraction", Analytical Biochemistry, 162, 1987, pp. 156-159.

George M. Church et al., "Genomic Sequencing", Proc. Natl. Acad. Sci., vol. 81, Apr. 1984, pp. 1991-1995.

Jean-Bernard Denault et al., "Furin/Pace/SPC1 : A Convertase Involved in Exocytic and Endocytic Processing of Precursor Proteins", FEBS Letters, 379, 1996, pp. 113-116.

Flanagan et al., "Alkaline Phosphatase Fusions of Ligands or Receptors as in Situ Probes for Staining of Cells, Tissues, and Embryos", Methods in Enzymology (2000) 327:19-35.

Flanagan et al., "Alkaline Phosphatase Fusion Proteins for Molecular Characterization and Cloning of Receptors and Their Ligands", Methods in Enzymology (2000) 327:198-210.

Flanagan et al., "The kit Ligand: A Cell Surface Molecule Altered in Steel Mutant Fibroblasts", Cell (1990) 63:185-194.

Fletcher et al., "Atrial natriuretic factor receptors and stimulation of cyclic GMP formation in normal and malignant osteoblasts", FEBS (1986) 208(2):263-268.

Fujishige et al., "Alteration of cGMP metabolism during chondrogenic differentiation of chondroprogenitor-like EC cells, ATDC5", Biochimica et Biophysica Acta (1999) 1452:219-227.

Hagiwara et al., "Change in the Expression of C-Type Natriuretic Peptide and Its Receptor, B-TypeNatriuretic Peptide Receptor, during Dedifferentiation of Chondrocytes into Fibroblast-Like Cells", J. Biochem. (1996) 119:264-267.

Hagiwara et al., "cGMP produced in response to ANP and CNP regulates proliferation and differentiation of osteoblastic cells", Am. J. Physiol.—Cell Physiology (1996) 39: C1311-C1318.

Hagiwara et al., "Autocrine Regulation of Rat Chondrocyte Proliferation by Natriuretic Peptide C and Its Receptor, Natriuretic Peptide Rector-B", The Journal of Biological Chemistry (1994) 269(14): 10729-10733.

He et al., "Allosteric Activation of a Spring-Loaded Natriuretic Peptide Receptor Dimer by Hormone", Science (2001) 293:1657-1662.

Hirata et al., "Binding, Internalization, and Degradation of Atrial Natriuretic Peptide in Cultured Vascular Smooth Muscle Cells of Rat", Biochemical and Biophysical Research Communications (1985) 132(3):976-984.

Hirata et al., "Vascular Receptor Binding Activities and Cyclic GMP Responses by Synthetic Human and Rat Atrial Natriuretic Peptides (ANP) and Receptor Down-Regulation by ANP", Biochemical and Biophysical Research Communications (1985) 128(2):538-546.

Hirata et al., "Specific Binding Sites for Atrial Natriuretic Peptide (ANP) in Cultured Mesenchymal Nonmyocardial Cells from Rat Heart", Biochemical and Biophysical Research Communications (1985) 131(1):222-229.

Hirata et al., "Effect of Synthetic Human Atrial Natriuretic Peptide on Aldosterone Secretion by Dispersed Aldosterone-Producing Adenoma Cells in Vitro", Journal of Clinical Endocrinology and Metabolism (1985) 61(4):677-680.

Hirose et al., "Comparative molecular biology of natriuretic peptide receptors", Can. J. Physiol. Pharmacol. (2001) 79:665-672.

Inoue et al., "Stimulation by C-Type Natriuretic Peptide of the Differentiation of Clonal Osteoblastic Mc3T3-E1 Cells", Biochemical and Biophysical Research Communications (1996) 221:703-707.

Inoue et al., "Stimulation by Retinoids of the Natriuretic Peptide System of Osteoblastic MC3T3-E1 Cells", Biochemical and Biophysical Research Communications (1996) 228:182-186.

Jaubert et al., "Three new allelic mouse mutations that cause skeletal overgrowth involve the natriuretic peptide receptor C gene (Npr3)", Proc. Natl. Acad. Sci. USA (1999) 96:10278-10283.

John et al., "Genetic Decreases in Atrial Natriuretic Peptide and Salt-Sensitive Hypertension", Science (1995) 267:679-681.

Kaneki et al., "Age-Related Changes in Bone Formation in Response to C-Type Natriuretic Peptide (CNP) and the Expression of Receptors for CNP in the Cultures of Calvarial Cells from Rats of Various Ages", ASBMR 23rd Annual Meeting (2001) Abstract No. M272.

Koyama et al., "AP-811, a novel ANP-C receptor selective agonist", Int. J. Peptide Protein Res. (1994) 43:332-336.

Levin, "Natriuretic peptide C-receptor: more than a clearance receptor", Endocrinology and Metabolism (1993) 264:E483-E489.

Levin et al., "Natriuretic Peptides", The New England Journal of Medicine (1998) 339(5):321-329.

Maack et al., "Physiological Role of Silent Receptors of Atrial Natriuretic Factor", Science (1987) 238:675-678.

Matsukawa et al., "The natriuretic peptide clearance receptor locally modulates the physiological effects of the natriuretic peptide system", Proc. Natl. Acad. Sci. USA (1999) 96:7403-7408.

Matsuo, "Discovery of a natriuretic peptide family and their clinical application", Can. J. Physiol. Pharmacol. (2001) 79:736-740.

Misono et al., "Rat Atrial Natriuretic Factor: Complete Amino Acid Sequence and Disulfide Linkage Essential for Biological Activity", Biochemical and Biophysical Research Communications (1984) 119(2):524-529.

Misono et al., "Rat Atrial Natriuretic Factor: Isolation, Structure and Biological Activities of Four Major Peptides", Biochemical and Biophysical Research Communications (1984) 123(2):444-451.

Miyazawa et al., "Cyclic GMP-Dependent Protein Kinase II Plays a Critical Role in C-Type Natriuretic Peptide-Mediated Endochondral Ossification", Endocrinology (2002) 143(9):3604-3610.

Moss, "Studies of the Acellular Bone of Teleost Fish", *Acta anat.* (1965) 60:262-276.

Nashida et al., "Characterization of Natriuretic Peptide Receptors in the Rat Parotid", *Biochemistry and Molecular Biology International* (1996) 40(1): 111-118.

Nishimoto et al., "Structure, Activity, and Distribution of Fish Osteocalcin", *The Journal of Biological Chemistry* (2003) 278(14):11843-11848.

Nishizawa et al., "Musclin, a Novel Skeletal Muscle-derived Secretory Factor", *The Journal of Biological Chemistry* (2004) 279(19): 19391-19395.

Olney, "Regulation of Bone Mass by Growth Hormone", *Med Pediatr Oncol* (2003) 41:228-234.

Pagano et al., "Cytoplasmic Domain of Natriuretic Peptide Receptor C Constitutes $G_i$ Activator Sequences that Inhibit Adenylyl Cyclase Activity", *The Journal of Biological Chemistry* (2001) 276(25):22064-22070.

Rose et al., "Effects of C-type natriuretic peptide on ionic currents in mouse sinoatrial node: a role for the NPR-C receptor", *Am J Physiol Heart Circ Physiol* (2004) 286:H1970-H1977.

Shukunami et al., "Chondrogenic Differentiation of Clonal Mouse Embryonic Cell Line ATDC5 In Vitro: Differentiation-dependent Gene Expression of Parathyroid Hormone (PTH)/PTH-related Peptide Receptor", *The Journal of Cell Biology* (1996) 133(2):457-468.

Smyth et al., "Effects of the ANF-C Receptor Ligand des[Cys105,Cys21]rANF(104-126) on ANF Internalization and cGMP Production by Bovine Pulmonary Artery Endothelial Cells", *Life Sciences* (1994) 54:1-7.

Suda et al., "C-Type Natriuretic Peptide/Guanylate Cyclase B System in Rat Osteogenic ROB-C26 Cells and its Down-Regulation by Dexamethazone", *Calcif Tissue Int* (1999) 65:472-478.

Suda et al., "Skeletal growth in transgenic mice that overexpress brain natriuretic peptide", *Proc. Natl. Acad. Sci USA* (1998) 95:2337-2342.

Suda et al., "C-Type Natriuretic Peptide as an Autocrine/Paracrine Regulator of Osteoblast", *Biochemical and Biophysical Research Communications* (1996) 223:1-6.

Suda et al., "C-type natriuretic peptide/guanylate cyclase B system in ATDC5 cells, a chondrogenic cell line", *J Bone Miner Metab* (2002) 20:136-141.

Suga et al., "Characterization of Natriuretic Peptide Receptors in Cultured Cells", *Hypertension* (1992) 19(6):762-765.

Tamura et al., "Cardiac fibrosis in mice lacking brain natriuretic peptide", *PNAS* (2000) 97(8):4239-4244.

Thomas et al., "Osteocrin, a Novel Bone-specific Secreted Protein That Modulates the Osteoblast Phenotype", *The Journal of Biological Chemistry* (2003) 278(50):50563-50571.

Veale et al., "The Discovery of Non-Basic Atrial Natriuretic Peptide Clearance Receptor Antagonists, Part I", *Bioorganic & Medicinal Chemistry Letters* (2000) 10:1949-1952.

Yamashita et al., "Concentration of mRNA for the Natriuretic Peptide Receptor-C in Hypertrophic Chondrocytes of the Fetal Mouse Tibia", *J. Biochem.* (2000) 127:177-179.

Yanaka et al., "1,25-Dihydroxyvitamin $D_3$ upregulates natriuretic peptide receptor-C expression in mouse osteoblasts", *American Journal of Physiology—Endocrinology* (1998) 275:E965-E973.

Yanaka et al., "Isolation and Characterization of the 5'-Flanking Regulatory Region of the Human Natriuretic Peptide Receptor C Gene", *Endocrinology* (1998) 139(3): 1389-1400.

Yasoda et al., "Overexpression of CNP in chondrocytes rescues achondroplasia through a MARK-dependent pathway", *Nature Medicine* (2004) 10(1):80-86.

Yasoda et al., "Natriuretic Peptide Regulation of Endochondral Ossification", *The Journal of Biological Chemistry* (1998) 273(19):11695-11700.

Anand-Srivasta et al., "Ring-deleted Analogs of Atrial Natriuretic Factor Inhibit Adenylate Cyclase/cAMP System", *The Journal of Biological Chemistry* (1990) 265(15):8566-8572.

Bartels et al., "Mutations in the Transmembrane Natriuretic Peptide Receptor NPR-B Impair Skeletal Growth and Cause Acromesomelic Dysplasia, Type Maroteaux", *Am. J. Hum. Genet.* (2004) 75:27-34.

Bord et al., "Characterization of Osteocrin Expression in Human Bone", *Journal of Histochemistry & Cytochemistry* (2005) 53(10):1181-1187.

Bourque et al., "A Histological Processing Technique that Preserves the Integrity of Calcified Tissues (Bone, Enamel), Yolky Amphibian Embryos, and Growth Factor Antigens in Skeletal Tissue", *The Journal of Histochemistry and Cytochemistry* (1993) 41(9):1429-1334.

Chauhan et al., "Release of C-type natriuretic peptide accounts for the biological activity of endothelium-derived hyperpolarizing factor", *PNAS* (2003) 100(3):1426-1431.

Chusho et al., "C-Type Natriuretic Peptide (CNP) as Novel Positive Regulator of Endochondral Ossification - The Analysis of CNP Knock Out Mice", *ASBMR 23rd Annual Meeting* (2001) Abstract No. 1013.

Chuso et al. "Dwarfism and early death in mice lacking C-type natriuretic peptide", *PNAS* (2001) 98(7):4016-4021.

Colvin et al., "Skeletal overgrowth and defeness in mice lacking fibroblast growth factor receptor 3", *Nature Genetics* (1996) 12:390-397.

Dacic et al., "Col1a1-Driven Transgenic Markers of Osteoblast Lineage Progression", *Journal of Bone and Mineral Research* (2001) 16(7):1228-1236.

Figure 1
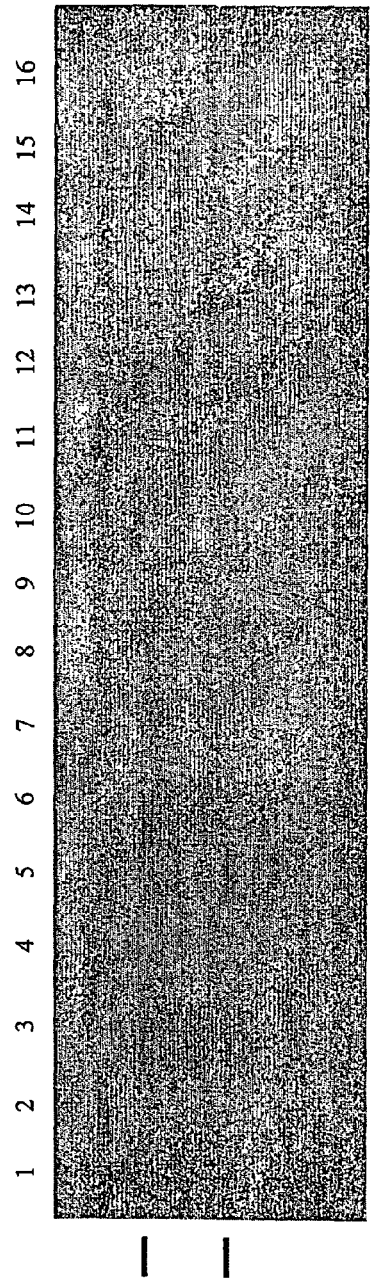
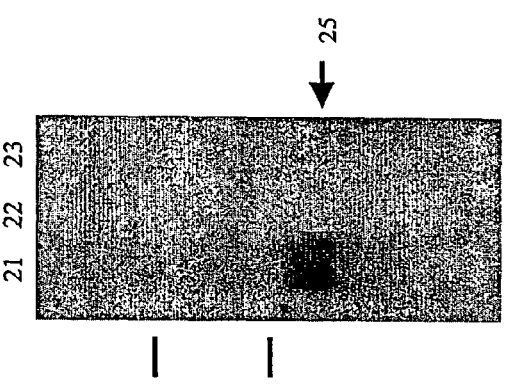

Figure 2

```
   1  gctaagtttg ggataagctg caggcgggac tccaaagtta ggagctctga cttctcacaa
  61  gATGCTGGAC TGGAGATTGG CAAGTACACA CTTCATCCTG GCTATGATTG TGATGCTGTG
 121  GGGCTCAGGA AAGGCATTCT CTGTGGACTT AGCATCACAG GAGTTTGGAA CAGCAAGCTT
 181  GCAGTCTCCA CCCACAGCCA GAGAAGAGAA GTCAGCCACT GAGCTTTCGG CTAAGCTCCT
 241  GCGTCTTGAT GATCTGGTGT CCTTAGAGAA TGACGTATTT GAGACCAAGA AAAAGAGAAG
 301  CTTCTCTGGC TTTGGGTCTC CCCTTGACAG ACTCTCAGCT GGGTCTGTAG AGCATAGAGG
 361  GAAACAAAGG AAAGCAGTAG ATCATTCAAA AAAGCGGTTT GGTATTCCCA TGGATCGGAT
 421  TGGTAGAAAC CGGCTCTCCA GTTCCAGAGG CTGAtggatt cttattgtgc gacttacttg
 481  tgtgagatgg cacagaacta tagaagacac ttcagtgaag ttcactaccc cttttgtcaa
 541  ggaattggcc tttcgcaaac cttcccaaag cttgatcctc cccagaccat cacgtcatag
 601  tgttgctgtg gttttagttg agttgtgcag atcatttcag tgcatggata tctctgaaag
 661  tatttttcaa tgattcccaa attgtaacgt ggccccctgaa cctactttt taaacagcag
 721  accaatataa tgcattctct tgccattaat attttcacat ttcagttaat caatgtgctt
 781  tctagaaacc tagtgtctga agatctgatg atctaaagaa atcagaaatg agcacatggt
 841  gattatata ggtttcttta gtttttctga gtttgtcga attgttgtaa acttcaactt
 901  caagcttaga aaaagacat tacatgagtg tttgcttcaa ctgtgtcaga gggcaaataa
 961  attttgagaa acctgagcaa ttgtgttctt taggaactaa taaaggatag tataattggc
1021  ccatatgtaa tattctgaca aactctgaat gtaaaagact catttgaaaa gaagttactg
1081  cctgccttgt ttacttctac cagcctaggg gtgaattgtt caaatgtttc ctatgttagc
1141  agcttttctt cttctttttt ttctttctat tttacttttt ttcttcattc aatgtttata
1201  agctaaaaat ccaaccaaat agtgcttgt gctttaaaag gggtattaa aatcaacatt
1261  aatctaaaaa aaaaaaaaaa
```

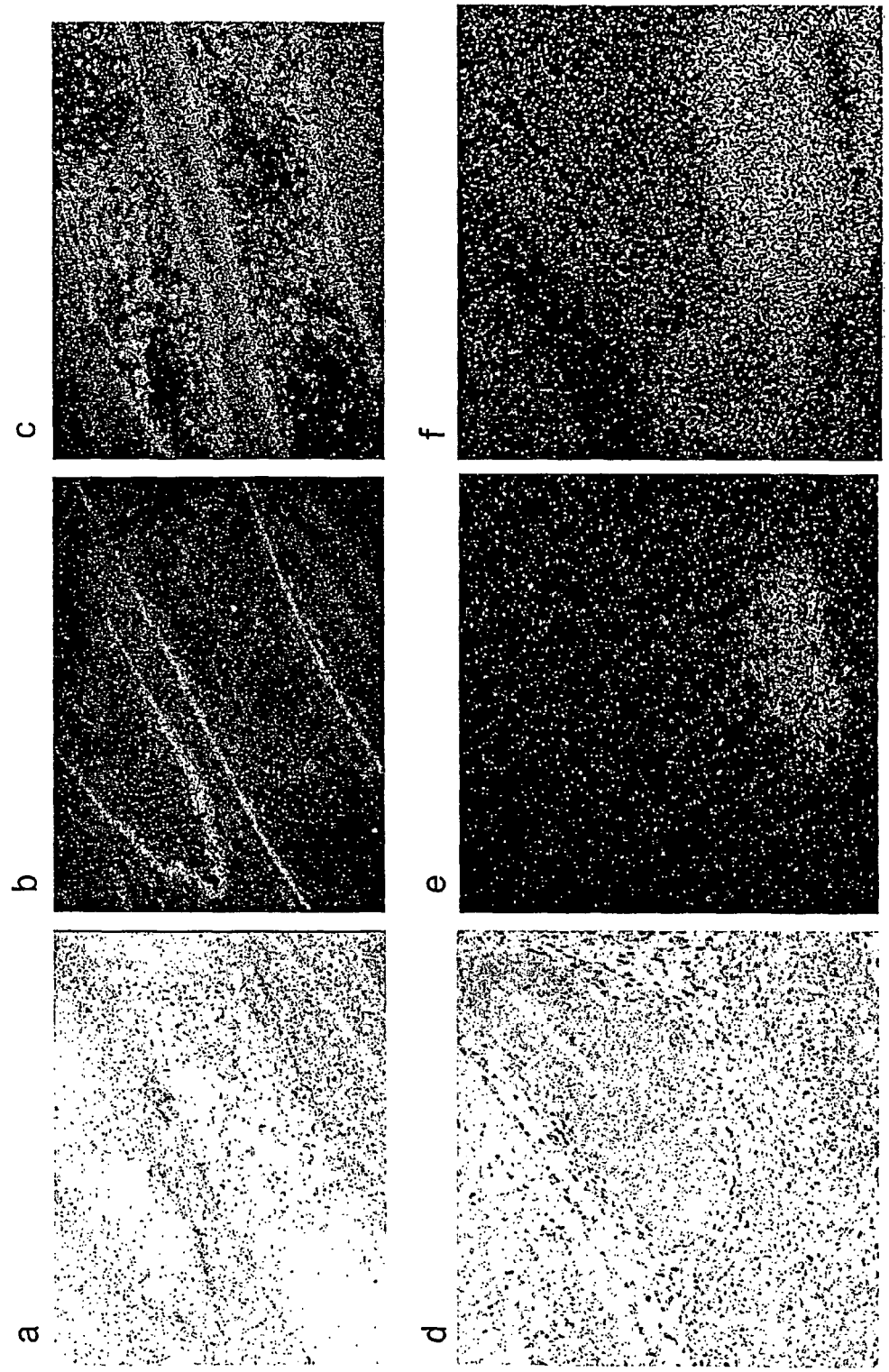

Figure 4

```
            1                                                            60
BP-1 ORF Human    (1) ATGCTGGACTGGAGAGATTGGCAAGTGCACATTTCATCCTGGCTGTGACACTGACACTGTGG
BP-1 ORF Bovine   (1) ATGCTGGACTGGAGAGATTGGCAAGTGCACATTTATCCTGGCTATGACACTGATGCTCTGG
BP-1 ORF Mouse    (1) ATGCTGGACTGGAGAGATTGGCAAGTACACACTTCATCCTGGCTATGATTGTGATGCTGTGG
BP-1 ORF Rat      (1) ATGCTGGACTGGAGAGATTGGCAAGTGCACACTTCCTCCTGGCTATGATCCTGATGCTGTGG
BP-1 ORF Chicken  (1) ATGCTGCAGTTCCAGCTTGTTGTGGTCCATCTGGCCCTTGTGATCACCCTGCAGTGG Consensus         (1) ATGCTGGACTGGAGAGATTGGCAAGTGCACATTTCATCCTGGCTATGAC CTGATGCTGTGG 61                                                          120
BP-1 ORF Human   (61) AGCTCAGGAAAAGTCCCTCTCAGTAGATGTAACAACAACAGAGAGGCCTTTGAT---TCTGGA
BP-1 ORF Bovine  (61) AGCTCAGGAAAAGTGTTCTCAGTGGGTGTCACAACA---GAGGCCTTTGAT---TCTGGA
BP-1 ORF Mouse   (61) GGCTCAGGAAAGGCCATTCTCTGTGACTTAGCATCA---CAGG------AG---TTTGGA
BP-1 ORF Rat     (61) GGCTCAGGAAAGGCCATTCTCCGTGACTTAGCATCA---GAGGCCTCCGAG---TTTGGA
BP-1 ORF Chicken (61) CATTCTAGTTCAGTGCTCCTTGCAGAGGCAGCTCCA---GAGCCTTTGGAGCCTTCTGCT Consensus        (61) GCTCAGGAAAAGT TTCTC GTGGA GTAGCA CA    GAGGCCTT GAG   TCTGGA
```

Figure 4 (continued)

```
                      121                                                        180
BP-1 ORF Human   (118) GTCATAGATGTGCAGTCAACACCCACAGTCAGGGAAGAGAAATCAGCCACTGACCTGACA
BP-1 ORF Bovine  (115) GTCTTAGGTGTGTTCAGTCATCACCCACAGTCAGAGAAGCGAAGTCGGCCACTGACCTGGCA
BP-1 ORF Mouse   (109) ACAGCAAGCTTGCAGTCTCCACCCACAGCCAGAAGAGAAGTCAGCCACTGAGCTTTCG
BP-1 ORF Rat     (115) GCAGAAAGCTTGCAGTCCCCACCCACAACCAGAGAAGAAGTCAGCCACGGAGCTTGCA
BP-1 ORF Chicken (118) GCTCTGGGCATGGCAGCACATCCTACTGCCAGCGAGGAGAAGTCAGCCTCCAGCCTGGCA
BP-1 ORF Python    (1)                             TACGGGCTGGAGGAGAAGTCGGCTACTGACCTGGTG
Consensus        (121) GC    TAGGC TGCAGTCACCACCCACAGCCAGAGAGAAGTCAGCCCACTGACCTGGCA 181                                                        240
BP-1 ORF Human   (178) GCAAAACTCTTGCTTCTTGATGAATTGGTGTCCCTAGAAAATGATGTGATTGAGACAAAG
BP-1 ORF Bovine  (175) GCAAAACTCTTACTTCTTGATGAATTGGTGTCTCTGGAGAATGACGTGATTGAAACAAAG
BP-1 ORF Mouse   (169) GCTAAGCTCCTGCGTCTTGATGATCGGTTCTTGGTGTCCTTAGAGAATGACGTATTGAGACCAAG
BP-1 ORF Rat     (175) GCTAAGCTCCTGCTTCTTGATGATCGGTTCTTGGTGTCCTTGGAGAATGATGTGTTTGAGACCAAG
BP-1 ORF Chicken (178) GCCAAACTGCTCCTTCTTGATGAGTTGGTGTCTCTGGAGAATGAGGTAACTGAGACAAAG
BP-1 ORF Python   (38) GCCAAATTTGCTCCTCAACGAATTGGTGTCCCTTGAAAACGATGTCTTTGAGACCAAG
Consensus        (181) GC AAACTCTTCTTGATGAATTGGTGTCCCTGGAGAATGATGTGTTTGAGACCAAG
```

Figure 4 (continued)

```
                           241                                                           300
BP-1 ORF Human    (238)  AAGAAAAAGGAGTTTCTCTGGTTTTGGGTCTCCCCCTTGACAGAGACTCTCAGCTGGCTCTGTA
BP-1 ORF Bovine   (235)  AAGAAAAAGAAGCTTCTCTGGGTTTGGTTCTCCCCTTGACAGAGACTCTCAGCTGGCTCTGTA
BP-1 ORF Mouse    (229)  AAAAAGAGAAGAGCTTCTCTGGCTCTGGGTCTCCCCTTGACAGAGACTCTCAGCTGGGTCTGTA
BP-1 ORF Rat      (235)  AAGAAGAGAAGAGCTTCTCTGGCTTCGGGTCTCCCCTTGACAGAGACTCTCGGCTGGGTCTGTA
BP-1 ORF Chicken  (238)  AAGAAAAAGAAGTTTTCCAGGATTTGGCTCCCCGATCGACAGAATTCTGCGACATCTGTG
BP-1 ORF Python    (98)  AAGAGAGAGAGCTTCTCCGGGTTTGGCTCCCCACTTGACAGACTTTCGG-TGGGCCTG--
Consensus         (241)  AAGAAGAGAAGAAGCTTCTCTGG  TTTGGGTCTCCCCCTTGACAGAGACTCTCAGCTGGGTCTGTA 301                                                           360
BP-1 ORF Human    (298)  GATCACAAAGGTAAACAGAGGAGGAAAGTAGTAGATCATCATCCAAAAAGGCGATTTGGTATCCCC
BP-1 ORF Bovine   (295)  AGTCATAAAGGTAAACAGAGGAGGAAAGTAGTAGATCATCATCCAAAAAGGCGATTTGGTATCCCT
BP-1 ORF Mouse    (289)  GAGCATAGAGGGAAACAAAGGAGACAAAGGAGAAAGCAGTAGATCATCATTCAAAAAAAGCCGGTTTGGTATTCCC
BP-1 ORF Rat      (295)  GAGCATAGAGGGAAACAAAAGGAGACAAAAGGAGAGTAGTTGATCATCATTCAAAAAAAGCCGATTTGGTATTCCC
BP-1 ORF Chicken  (298)  GATGCTAAAGGCAAACAGAGGAAAGTGGTTGAGCTGCCTAAGAGACGGTTTGGAGTTCCT
BP-1 ORF Python   (155)  -----AAAGCCAAGCAGAGGAAAGCTCTGGAGCTGCCAAAGAAGCGGTTTGGATTCCT
Consensus         (301)  GATCATAAAGG AAACAGAGAGGAAAGTAGTAGATCATCAGAGAAAAGGCGGTTTGGTATTCCT
```

Figure 4 (continued)

```
                    361                                            405
BP-1 ORF Human    (358) ATGGATCGGATTGGTAGAAACCGGCTTTCAAATTCCAGAGGCTAA
BP-1 ORF Bovine   (355) ATGGATCGGATTGGAAGAAACCGGCTTTCAAATTCCAGAGGCTAA
BP-1 ORF Mouse    (349) ATGGATCGGATTGGTAGAAACCGGCTCTCCAGTTCCAGAGGCTGA
BP-1 ORF Rat      (355) ATGGATCGAATTGGTAGAAACCGTCTCTCCAGTTCCAGGGGCTGA
BP-1 ORF Chicken  (358) CTTGACCGGATCGGAGTGAGTCGTCTGTTGGCAACACCAAGGGTTAG
BP-1 ORF Python   (209) CTAGATCGGATTGGCGTGAATCGTTTGAGCGGCTCCAGAGGTTAG
Consensus         (361) ATGGATCGGATTGGTAGAAACCGTCTTTCCAGTTCCAGAGGCTAA
```

Figure 5A

| | | |
|---|---|---|
| Homo sapiens | (1) | MLDWRLASAHFILAVTLTLMSSGKVLSVDVTTTEAFDSGVIDVQSTPTVR |
| Bos taurus | (1) | MLDWRLASAHFILAMTLMLWSSGKVFSVGVTT-EAFDSGVLGVQSSPTVR |
| Mus musculus | (1) | MLDWRLASTHFILAMIVMLWGSGKAFSVDLAS-QEFGTASLQS--PPTAR |
| Rattus norvegicus | (1) | MLDWRLASAHFLLAMILMLWGSGKAFSVDLAS-EASEFGAESLQSPPTTR |
| Gallus gallus | (1) | MLQFQLVVVHLALVITLLQWHSSSVLLAEAAPEPLEPSAALGMAAHPTAS |
| Python molurus bivittatus | | |
| Consensus | (1) | MLDWRLASAHFILAMTLMLW-SGKVFSVDLASE---DSG-L-LQS-PT-R |

| | | | | |
|---|---|---|---|---|
| Homo sapiens | (51) | EEKSATDLTAKLLLLDELVSLENDVIET | KKKR | SFSGFGSPLDRLSAGSVD |
| Bos taurus | (50) | EAKSATDLAAKLLLLDELVSLENDVIET | KKKR | SFSGFGSPLDRLSAGSVS |
| Mus musculus | (48) | EEKSATELSAKLLRLDDLIVSLENDVFET | KKKR | SFSGFGSPLDRLSAGSVE |
| Rattus norvegicus | (50) | EEKSATELAAKLLLLDDLVSLENDVFET | KKKR | SFSGFGSPLDRLSAGSVE |
| Gallus gallus | (51) | EEKSASSLAAKLLLLDELVSLENEVTET | KKKR | SFPGFGSPIDRISATSVD |
| Python molurus bivittatus | | TDLVAKILLLNELVISLENDVFET | KKKR | SFSGFGSPLDRLSVG-L- |
| Consensus | (51) | EEKSATDLAAKLLLLDELVSLENDVFET | KKKR | SFSGFGSPLDRLSAGSVD |

| | | | | |
|---|---|---|---|---|
| Homo sapiens | (101) | HKG KQRK | VVDHP | KRR | FGIPMDRIGRNRLSNSRG- |
| Bos taurus | (100) | HKG KQRK | VVDHP | KRR | FGIPMDRIGRNRLSNSRG- |
| Mus musculus | (98) | HRG KQRK | AVDHS | KKR | FGIPMDRIGRNRLSSSRG- |
| Rattus norvegicus | (100) | HRG KQRR | VVDHS | KKR | FGIPMDRIGRNRLSSSRG- |
| Gallus gallus | (101) | AKG KQRK | VVELP | KRR | FGVPLDRIGVSRLSSSRG- |
| Python molurus bivittatus | | -KA KQRK | AVELP | KKR | FGIPLDRIGVNRLSGSRG |
| Consensus | (101) | HKG KQRK | VVDHP | KKR | FGIPMDRIGRNRLSNSRG- |

Figure 5B

| | | | | |
|---|---|---|---|---|
| Human | BP-1 | $C^{129}$ | $F^{116}$ G I P M D R I G$^{124}$ | |
| Rat | Atrial natriuretic factor | $C^{99}$ | F G G R I D R I G | A Q S G L G C$^{145}$ |
| Rat | Brain natriuretic factor | $C^{110}$ | F G Q K I D R I G | A V S R L G C$^{115}$ |
| Rat | C-type natriuretic factor | | F G L K L D R I G | S M S G L G C$^{126}$ |

Figure 7
A
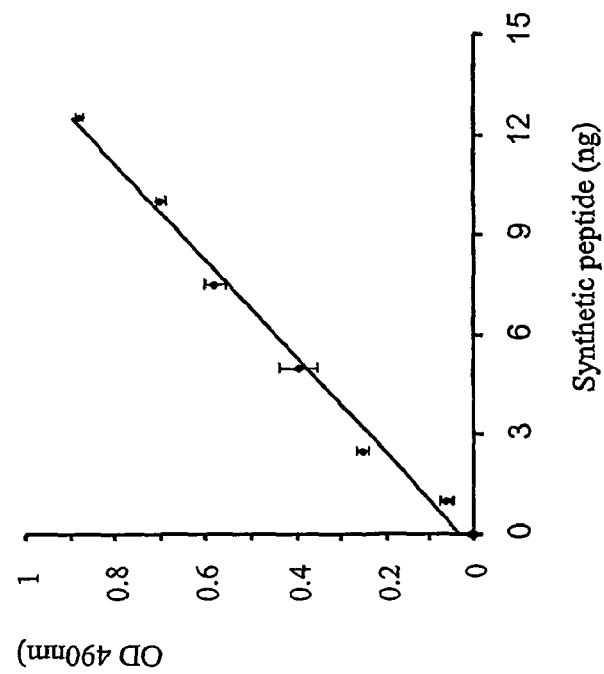
B
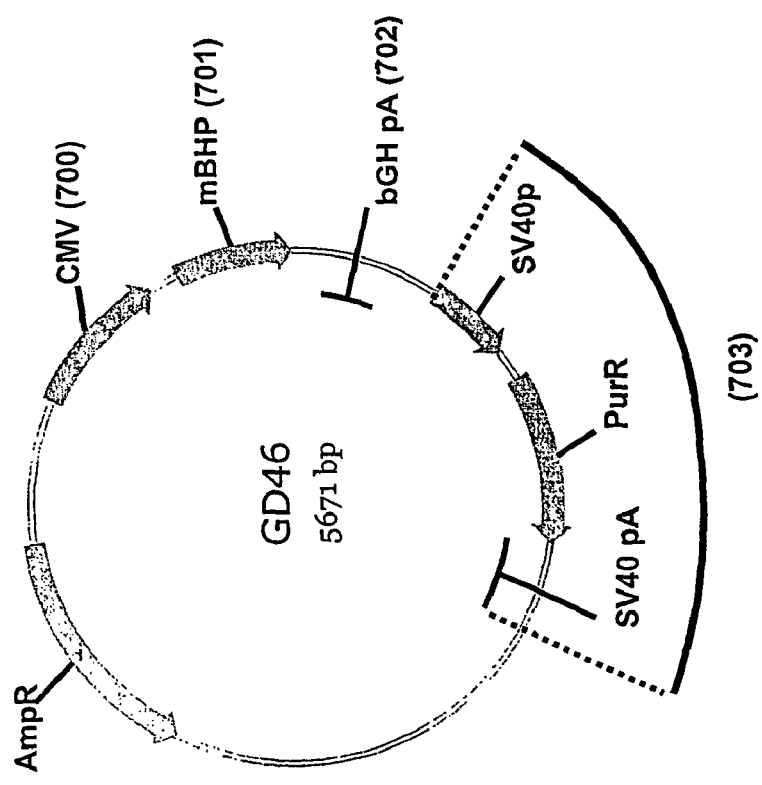

Figure 9
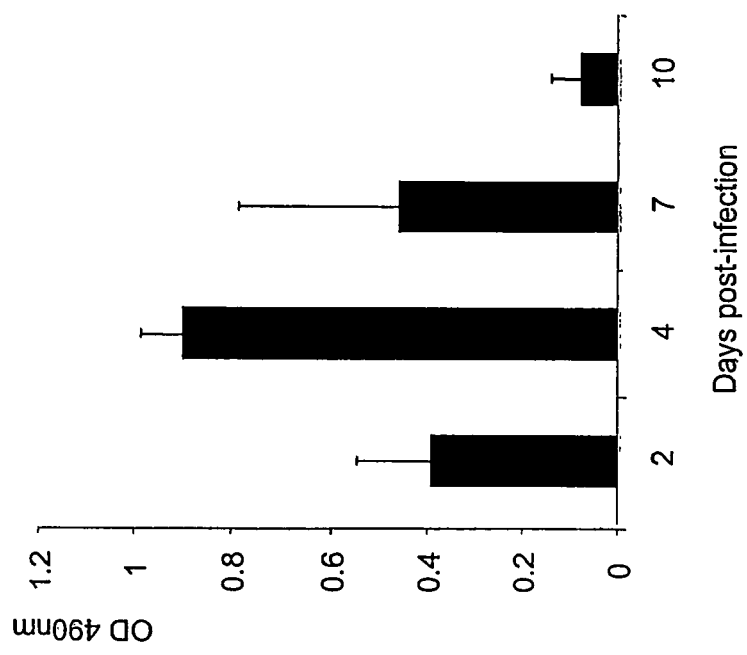
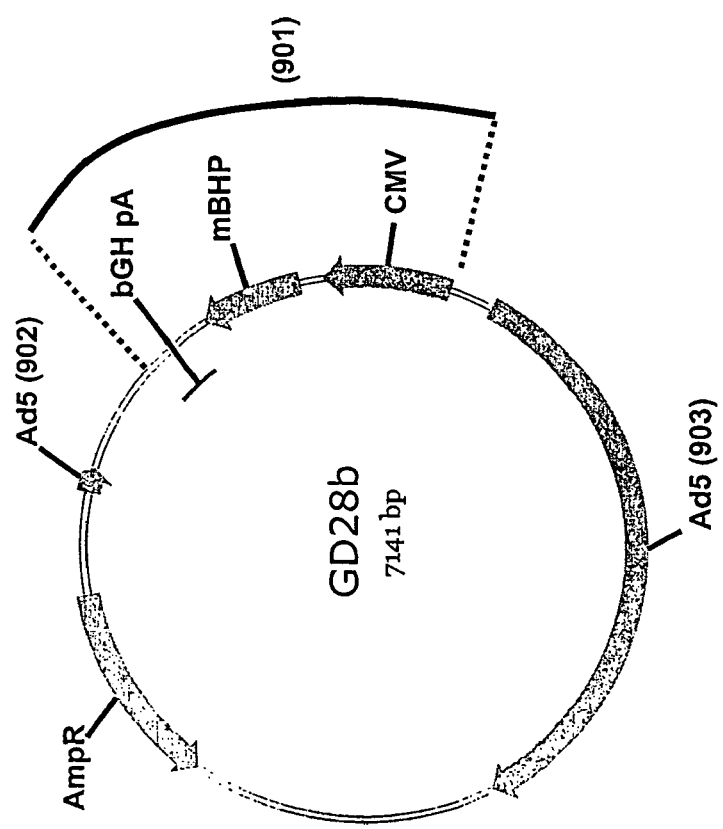

SEQUENCE LISTING

```
<160> NUMBER OF SEQ ID NOS: 45

<210> SEQ ID NO 1
<211> LENGTH: 1280
<212> TYPE: DNA
<213> ORGANISM: Mus musculus

<400> SEQUENCE: 1
gctaagtttg ggataagctg caggcgggac tccaaagtta ggagctctga cttctcacaa      60
gatgctggac tggagattgg caagtacaca cttcatcctg gctatgattg tgatgctgtg     120
gggctcagga aaggcattct ctgtggactt agcatcacag gagtttggaa cagcaagctt     180
gcagtctcca cccacagcca gagaagagaa gtcagccact gagctttcgg ctaagctcct     240
gcgtcttgat gatctggtgt ccttagagaa tgacgtattt gagaccaaga aaagagaag     300 cttctctggc tttgggtctc cccttgacag actctcagct gggtctgtag agcatagagg     360
```

```
gaaacaaagg aaagcagtag atcattcaaa aaagcggttt ggtattccca tggatcggat      420
tggtagaaac cggctctcca gttccagagg ctgatggatt cttattgtgc gacttacttg      480
tgtgagatgg cacagaacta tagaagacac ttcagtgaag ttcactaccc cttttgtcaa      540
ggaattggcc tttcgcaaac cttcccaaag cttgatcctc cccagaccat acgtcatag       600 tgttgctgtg gttttagttg agttgtgcag atcatttcag tgcatggata tctctgaaag      660 tattttcaa tgattcccaa attgtaacgt ggcccctgaa cctactttt ttaaacagca        720 gaccaatata atgcattctc ttgccattaa tattttcaca tttcagttaa tcaatgtgct      780
ttctagaaac ctagtgtctg aagatctgat gatctaaaga aatcagaaat gagcacatgg     840
tgatttatat aggtttcttt agttttctg aggtttgtcg aattgttgta aacttcaact       900
tcaagcttag aaaaaagaca ttacatgagt gtttgcttca actgtgtcag agggcaaata      960
aattttgaga aacctgagca attgtgttct ttaggaacta taaaggata gtataattgg      1020 cccatatgta atattctgac aaactctgaa tgtaaaagac tcatttgaaa agaagttact     1080
gcctggcttg tttacttcta ccagcctagg ggtgaattgt tcaaatgttt cctatgttag     1140
cagcttttct tcttcttttt tttctttcta ttttactttt tttcttcatt caatgtttat     1200
aagctaaaaa tccaaccaaa tagtgctttg tgctttaaaa gggggtatta aaatcaacat     1260
taatctaaaa aaaaaaaaaa                                                 1280

<210> SEQ ID NO 2
<211> LENGTH: 402
<212> TYPE: DNA
<213> ORGANISM: Homo sapiens

<400> SEQUENCE: 2
atgctggact ggagattggc aagtgcacat ttcatcctgg ctgtgacact gacactgtgg       60
agctcaggaa aagtcctctc agtagatgta acaacaacag aggcctttga ttctggagtc     120
atagatgtgc agtcaacacc cacagtcagg gaagagaaat cagccactga cctgacagca    180
aaactcttgc ttcttgatga attggtgtcc ctagaaaatg atgtgattga acaaagaag      240 aaaaggagtt ctctctggttt tgggtctccc cttgacagac tctcagctgg ctctgtagat    300
cacaaaggta acagaggaa agtagtagat catccaaaaa ggcgatttgg tatccccatg     360
gatcggattg gtagaaaccg gctttcaaat tccagaggct aa                        402

<210> SEQ ID NO 3
<211> LENGTH: 393
<212> TYPE: DNA
<213> ORGANISM: Mus musculus

<400> SEQUENCE: 3
atgctggact ggagattggc aagtacacac ttcatcctgg ctatgattgt gatgctgtgg      60
ggctcaggaa aggcattctc tgtggactta gcatcacagg agtttggaac agcaagcttg    120
cagtctccac ccacagccag agaagagaag tcagccactg agctttcggc taagctcctg    180
cgtcttgatg atctggtgtc cttagagaat gacgtatttg agaccaagaa aaagagaagc    240
ttctctggct ttgggtctcc ccttgacaga ctctcagctg gtctgtaga gcatagaggg     300 aaacaaagga aagcagtaga tcattcaaaa aagcggtttg gtattcccat ggatcggatt    360
ggtagaaacc ggctctccag ttccagaggc tga                                  393

<210> SEQ ID NO 4
```

```
<211> LENGTH: 399
<212> TYPE: DNA
<213> ORGANISM: Rattus norvegicus

<400> SEQUENCE: 4
atgctggact ggagattggc aagtgcacac ttcctcctgg ctatgatcct gatgctgtgg      60
ggctcaggaa aggcattctc cgtggactta gcatcagagg cctccgagtt tggagcagaa     120
agcttgcagt ccccacccac aaccagagaa gagaagtcag ccacggagct tgcagctaag     180
ctcctgcttc ttgatgatct ggtgtccttg gagaatgatg tgtttgagac caagaagaag     240
agaagcttct ctggcttcgg gtctcccctt gacagactct cggctgggtc tgtagagcat     300
agagggaaac aaaggagagt agttgatcat tcaaaaaagc gatttggtat tcccatggat     360
cgaattggta gaaaccgtct ctccagttcc aggggctga                            399

<210> SEQ ID NO 5
<211> LENGTH: 399
<212> TYPE: DNA
<213> ORGANISM: Bos taurus

<400> SEQUENCE: 5
atgctggact ggagattagc aagtgcacat tttatcctgg ctatgacact gatgctctgg      60
agctcaggaa aagtgttctc agtgggtgtc acaacagagg cctttgattc tggagtctta     120
ggtgttcagt catcacccac agtcagagaa gcgaagtcgg ccactgacct ggcagcaaaa     180
ctcttacttc ttgatgaact tgtgtctctg gagaatgacg tgattgaaac aaagaagaaa     240
agaagcttct ctgggtttgg ttctcccctg gacagactct cagctggctc tgtaagtcat     300
aaaggtaaac agaggaaagt agtagatcat ccaaaaaggc gatttggtat ccctatggat     360
cggattggaa gaaaccggct ttcaaattcc agaggctaa                            399

<210> SEQ ID NO 6
<211> LENGTH: 402
<212> TYPE: DNA
<213> ORGANISM: Gallus gallus

<400> SEQUENCE: 6
atgctgcagt ccagcttgt tgtggtccat ctggcccttg tgatcaccct gctgcagtgg        60
cattctagtt cagtgctcct tgcagaggca gctccagagc ctttggagcc ttctgctgct     120
ctgggcatgg cagcacatcc tactgccagc gaggagaagt cagcctccag cctggcagcc     180
aaactgctcc ttcttgatga gttggtgtct ctggagaatg aggtaactga dcaaagaag     240 aaaagaagtt ttccaggatt tggctccccg atcgacagaa tttctgcgac atctgtggat     300
gctaaaggca aacagaggaa agtggttgag ctgcctaaga dacggtttgg agttcctctt     360
gaccggatcg gagtgagtcg tcttggcaac accaagggtt ag                        402

<210> SEQ ID NO 7
<211> LENGTH: 253
<212> TYPE: DNA
<213> ORGANISM: Python molurus bivittatus

<400> SEQUENCE: 7
tacggcgtcg gaggagaagt cggctactga cctggtggcc aaaatttgc tcctcaacga       60 attggtgtcc cttgaaaacg atgtctttga gaccaagaag aagaggagct tctccgggtt     120
tggctcccca cttgacagac tttcggtggg cctgaaagcc aagcagagga aagctgtgga     180
gctgccaaag aagcggtttg ggattcctct agatcggatt ggcgtgaatc gtttgagcgg     240
```

```
<210> SEQ ID NO 8
<211> LENGTH: 405
<212> TYPE: DNA
<213> ORGANISM: Artificial Sequence
<220> FEATURE:
<223> OTHER INFORMATION: Consensus DNA sequence for BP-1
<220> FEATURE:
<221> NAME/KEY: misc_feature
<222> LOCATION: 48, 61, 75, 81, 87, 94, 97, 98, 99, 108, 112, 113,
      114, 123, 124, 130, 183, 261, 312
<223> OTHER INFORMATION: n = A,T,C or G

<400> SEQUENCE: 8
atgctggact ggagattggc aagtgcacat tcatcctgg ctatgacnct gatgctgtgg    60
ngctcaggaa aagtnttctc ngtggangta gcancannng aggccttnga gnnntctgga   120
gcnntaggcn tgcagtcacc acccacagcc agagaagaga agtcagccac tgacctggca   180
gcnaaactct tgcttcttga tgaattggtg tccctggaga atgatgtgtt tgagaccaag   240
aagaagagaa gcttctctgg ntttgggtct ccccttgaca gactctcagc tgggtctgta   300
gatcataaag gnaaacagag gaaagtagta gatcatccaa aaaggcggtt tggtattcct   360
atggatcgaa ttggtagaaa ccgtctttcc agttccagag gctaa                  405

<210> SEQ ID NO 9
<211> LENGTH: 133
<212> TYPE: PRT
<213> ORGANISM: Homo sapiens

<400> SEQUENCE: 9

Met Leu Asp Trp Arg Leu Ala Ser Ala His Phe Ile Leu Ala Val Thr
  1               5                  10                  15

Leu Thr Leu Trp Ser Ser Gly Lys Val Leu Ser Val Asp Val Thr Thr
             20                  25                  30

Thr Glu Ala Phe Asp Ser Gly Val Ile Asp Val Gln Ser Thr Pro Thr
         35                  40                  45

Val Arg Glu Glu Lys Ser Ala Thr Asp Leu Thr Ala Lys Leu Leu Leu
     50                  55                  60

Leu Asp Glu Leu Val Ser Leu Glu Asn Asp Val Ile Glu Thr Lys Lys
 65                  70                  75                  80

Lys Arg Ser Phe Ser Gly Phe Gly Ser Pro Leu Asp Arg Leu Ser Ala
                 85                  90                  95

Gly Ser Val Asp His Lys Gly Lys Gln Arg Lys Val Val Asp His Pro
            100                 105                 110

Lys Arg Arg Phe Gly Ile Pro Met Asp Arg Ile Gly Arg Asn Arg Leu
        115                 120                 125

Ser Asn Ser Arg Gly
    130

<210> SEQ ID NO 10
<211> LENGTH: 130
<212> TYPE: PRT
<213> ORGANISM: Mus musculus

<400> SEQUENCE: 10

Met Leu Asp Trp Arg Leu Ala Ser Thr His Phe Ile Leu Ala Met Ile
  1               5                  10                  15

Val Met Leu Trp Gly Ser Gly Lys Ala Phe Ser Val Asp Leu Ala Ser
```

-continued

```
                20                  25                  30
Gln Glu Phe Gly Thr Ala Ser Leu Gln Ser Pro Thr Ala Arg Glu
             35                  40                  45

Glu Lys Ser Ala Thr Glu Leu Ser Ala Lys Leu Leu Arg Leu Asp Asp
 50                  55                  60

Leu Val Ser Leu Glu Asn Asp Val Phe Glu Thr Lys Lys Arg Ser
 65                  70                  75                  80

Phe Ser Gly Phe Gly Ser Pro Leu Asp Arg Leu Ser Ala Gly Ser Val
                 85                  90                  95

Glu His Arg Gly Lys Gln Arg Lys Ala Val Asp His Ser Lys Lys Arg
                100                 105                 110

Phe Gly Ile Pro Met Asp Arg Ile Gly Arg Asn Arg Leu Ser Ser Ser
        115                 120                 125

Arg Gly
    130
```

<210> SEQ ID NO 11
<211> LENGTH: 132
<212> TYPE: PRT
<213> ORGANISM: Rattus norvegicus

<400> SEQUENCE: 11

```
Met Leu Asp Trp Arg Leu Ala Ser Ala His Phe Leu Leu Ala Met Ile
  1               5                  10                  15

Leu Met Leu Trp Gly Ser Gly Lys Ala Phe Ser Val Asp Leu Ala Ser
                 20                  25                  30

Glu Ala Ser Glu Phe Gly Ala Glu Ser Leu Gln Ser Pro Pro Thr Thr
             35                  40                  45

Arg Glu Glu Lys Ser Ala Thr Glu Leu Ala Ala Lys Leu Leu Leu Leu
 50                  55                  60

Asp Asp Leu Val Ser Leu Glu Asn Asp Val Phe Glu Thr Lys Lys Lys
 65                  70                  75                  80

Arg Ser Phe Ser Gly Phe Gly Ser Pro Leu Asp Arg Leu Ser Ala Gly
                 85                  90                  95

Ser Val Glu His Arg Gly Lys Gln Arg Arg Val Val Asp His Ser Lys
                100                 105                 110

Lys Arg Phe Gly Ile Pro Met Asp Arg Ile Gly Arg Asn Arg Leu Ser
        115                 120                 125

Ser Ser Arg Gly
    130
```

<210> SEQ ID NO 12
<211> LENGTH: 132
<212> TYPE: PRT
<213> ORGANISM: Bos taurus

<400> SEQUENCE: 12

```
Met Leu Asp Trp Arg Leu Ala Ser Ala His Phe Ile Leu Ala Met Thr
  1               5                  10                  15

Leu Met Leu Trp Ser Ser Gly Lys Val Phe Ser Val Gly Val Thr Thr
                 20                  25                  30

Glu Ala Phe Asp Ser Gly Val Leu Gly Val Gln Ser Ser Pro Thr Val
             35                  40                  45

Arg Glu Ala Lys Ser Ala Thr Asp Leu Ala Ala Lys Leu Leu Leu Leu
 50                  55                  60

Asp Glu Leu Val Ser Leu Glu Asn Asp Val Ile Glu Thr Lys Lys Lys
```

```
                      65                  70                  75                  80
Arg Ser Phe Ser Gly Phe Gly Ser Pro Leu Asp Arg Leu Ser Ala Gly
                    85                  90                  95

Ser Val Ser His Lys Gly Lys Gln Arg Lys Val Val Asp His Pro Lys
                100                 105                 110

Arg Arg Phe Gly Ile Pro Met Asp Arg Ile Gly Arg Asn Arg Leu Ser
            115                 120                 125

Asn Ser Arg Gly
        130

<210> SEQ ID NO 13
<211> LENGTH: 133
<212> TYPE: PRT
<213> ORGANISM: Gallus gallus

<400> SEQUENCE: 13

Met Leu Gln Phe Gln Leu Val Val His Leu Ala Leu Val Ile Thr
 1               5                  10                  15

Leu Leu Gln Trp His Ser Ser Val Leu Ala Glu Ala Ala Pro
                20                  25                  30

Glu Pro Leu Glu Pro Ser Ala Ala Leu Gly Met Ala Ala His Pro Thr
                35                  40                  45

Ala Ser Glu Glu Lys Ser Ala Ser Leu Ala Ala Lys Leu Leu Leu
 50                  55                  60

Leu Asp Glu Leu Val Ser Leu Glu Asn Glu Val Thr Glu Thr Lys Lys
65                  70                  75                  80

Lys Arg Ser Phe Pro Gly Phe Gly Ser Pro Ile Asp Arg Ile Ser Ala
                85                  90                  95

Thr Ser Val Asp Ala Lys Gly Lys Gln Arg Lys Val Val Glu Leu Pro
                100                 105                 110

Lys Arg Arg Phe Gly Val Pro Leu Asp Arg Ile Gly Val Ser Arg Leu
            115                 120                 125

Gly Asn Thr Lys Gly
        130

<210> SEQ ID NO 14
<211> LENGTH: 75
<212> TYPE: PRT
<213> ORGANISM: Python molurus bivittatus

<400> SEQUENCE: 14

Thr Asp Leu Val Ala Lys Ile Leu Leu Leu Asn Glu Leu Val Ser Leu
 1               5                  10                  15

Glu Asn Asp Val Phe Glu Thr Lys Lys Arg Ser Phe Ser Gly Phe
                20                  25                  30

Gly Ser Pro Leu Asp Arg Leu Ser Val Gly Leu Lys Ala Lys Gln Arg
            35                  40                  45

Lys Ala Val Glu Leu Pro Lys Lys Arg Phe Gly Ile Pro Leu Asp Arg
        50                  55                  60

Ile Gly Val Asn Arg Leu Ser Gly Ser Arg Gly
65                  70                  75

<210> SEQ ID NO 15
<211> LENGTH: 132
<212> TYPE: PRT
<213> ORGANISM: Artificial Sequence
<220> FEATURE:
<223> OTHER INFORMATION: Consensus polypeptide sequence for BP-1
```

```
<220> FEATURE:
<221> NAME/KEY: VARIANT
<222> LOCATION: 21, 34, 35, 36, 40, 42, 46, 49
<223> OTHER INFORMATION: Xaa = Any Amino Acid

<400> SEQUENCE: 15

Met Leu Asp Trp Arg Leu Ala Ser Ala His Phe Ile Leu Ala Met Thr
1               5                   10                  15

Leu Met Leu Trp Xaa Ser Gly Lys Val Phe Ser Val Asp Leu Ala Ser
            20                  25                  30

Glu Xaa Xaa Xaa Asp Ser Gly Xaa Leu Xaa Leu Gln Ser Xaa Pro Thr
        35                  40                  45

Xaa Glu Glu Lys Ser Ala Thr Asp Leu Ala Ala Lys Leu Leu Leu Leu
    50                  55                  60

Asp Glu Leu Val Ser Leu Glu Asn Asp Val Phe Glu Thr Lys Lys Lys
65                  70                  75                  80

Arg Ser Phe Ser Gly Phe Gly Ser Pro Leu Asp Arg Leu Ser Ala Gly
                85                  90                  95

Ser Val Asp His Lys Gly Lys Gln Arg Lys Val Val Asp His Pro Lys
            100                 105                 110

Lys Arg Phe Gly Ile Pro Met Asp Arg Ile Gly Arg Asn Arg Leu Ser
            115                 120                 125

Asn Ser Arg Gly
        130

<210> SEQ ID NO 16
<211> LENGTH: 9
<212> TYPE: PRT
<213> ORGANISM: Homo sapiens

<400> SEQUENCE: 16

Phe Gly Ile Pro Met Asp Arg Ile Gly
1               5

<210> SEQ ID NO 17
<211> LENGTH: 17
<212> TYPE: PRT
<213> ORGANISM: Rattus norvegicus

<400> SEQUENCE: 17

Cys Phe Gly Gly Arg Ile Asp Arg Ile Gly Ala Gln Ser Gly Leu Gly
1               5                   10                  15

Cys

<210> SEQ ID NO 18
<211> LENGTH: 17
<212> TYPE: PRT
<213> ORGANISM: Rattus norvegicus

<400> SEQUENCE: 18

Cys Phe Gly Gln Lys Ile Asp Arg Ile Gly Ala Val Ser Arg Leu Gly
1               5                   10                  15

Cys

<210> SEQ ID NO 19
<211> LENGTH: 17
<212> TYPE: PRT
<213> ORGANISM: Rattus norvegicus

<400> SEQUENCE: 19
```

```
Cys Phe Gly Leu Lys Leu Asp Arg Ile Gly Ser Met Ser Gly Leu Gly
 1               5                  10                  15

Cys
```

<210> SEQ ID NO 20
<211> LENGTH: 106
<212> TYPE: PRT
<213> ORGANISM: Homo sapiens

<400> SEQUENCE: 20

```
Val Asp Val Thr Thr Thr Glu Ala Phe Asp Ser Gly Val Ile Asp Val
 1               5                  10                  15

Gln Ser Thr Pro Thr Val Arg Glu Glu Lys Ser Ala Thr Asp Leu Thr
            20                  25                  30

Ala Lys Leu Leu Leu Leu Asp Glu Leu Val Ser Leu Glu Asn Asp Val
        35                  40                  45

Ile Glu Thr Lys Lys Lys Arg Ser Phe Ser Gly Phe Gly Ser Pro Leu
    50                  55                  60

Asp Arg Leu Ser Ala Gly Ser Val Asp His Lys Gly Lys Gln Arg Lys
65                  70                  75                  80

Val Val Asp His Pro Lys Arg Arg Phe Gly Ile Pro Met Asp Arg Ile
                85                  90                  95

Gly Arg Asn Arg Leu Ser Asn Ser Arg Gly
                100                 105
```

<210> SEQ ID NO 21
<211> LENGTH: 51
<212> TYPE: PRT
<213> ORGANISM: Homo sapiens

<400> SEQUENCE: 21

```
Ser Phe Ser Gly Phe Gly Ser Pro Leu Asp Arg Leu Ser Ala Gly Ser
 1               5                  10                  15

Val Asp His Lys Gly Lys Gln Arg Lys Val Val Asp His Pro Lys Arg
            20                  25                  30

Arg Phe Gly Ile Pro Met Asp Arg Ile Gly Arg Asn Arg Leu Ser Asn
        35                  40                  45

Ser Arg Gly
    50
```

<210> SEQ ID NO 22
<211> LENGTH: 30
<212> TYPE: PRT
<213> ORGANISM: Homo sapiens

<400> SEQUENCE: 22

```
Ser Phe Ser Gly Phe Gly Ser Pro Leu Asp Arg Leu Ser Ala Gly Ser
 1               5                  10                  15

Val Asp His Lys Gly Lys Gln Arg Lys Val Val Asp His Pro
            20                  25                  30
```

<210> SEQ ID NO 23
<211> LENGTH: 18
<212> TYPE: PRT
<213> ORGANISM: Homo sapiens

<400> SEQUENCE: 23

```
Phe Gly Ile Pro Met Asp Arg Ile Gly Arg Asn Arg Leu Ser Asn Ser
 1               5                  10                  15
```

Arg Gly

<210> SEQ ID NO 24
<211> LENGTH: 21
<212> TYPE: PRT
<213> ORGANISM: Homo sapiens

<400> SEQUENCE: 24

Ser Phe Ser Gly Phe Gly Ser Pro Leu Asp Arg Leu Ser Ala Gly Ser
1               5                   10                  15

Val Asp His Lys Gly
            20

<210> SEQ ID NO 25
<211> LENGTH: 26
<212> TYPE: PRT
<213> ORGANISM: Homo sapiens

<400> SEQUENCE: 25

Val Val Asp His Pro Lys Arg Arg Phe Gly Ile Pro Met Asp Arg Ile
1               5                   10                  15

Gly Arg Asn Arg Leu Ser Asn Ser Arg Gly
            20                  25

<210> SEQ ID NO 26
<211> LENGTH: 14
<212> TYPE: PRT
<213> ORGANISM: Homo sapiens

<400> SEQUENCE: 26

Asp Glu Leu Val Ser Leu Glu Asn Asp Val Ile Glu Thr Lys
1               5                   10

<210> SEQ ID NO 27
<211> LENGTH: 14
<212> TYPE: PRT
<213> ORGANISM: Homo sapiens

<400> SEQUENCE: 27

Arg Leu Ser Ala Gly Ser Val Asp His Lys Gly Lys Gln Arg
1               5                   10

<210> SEQ ID NO 28
<211> LENGTH: 14
<212> TYPE: PRT
<213> ORGANISM: Homo sapiens

<400> SEQUENCE: 28

Met Asp Arg Ile Gly Arg Asn Arg Leu Ser Asn Ser Arg Gly
1               5                   10

<210> SEQ ID NO 29
<211> LENGTH: 30
<212> TYPE: RNA
<213> ORGANISM: Artificial Sequence
<220> FEATURE:
<223> OTHER INFORMATION: Synthetic oligoribonucleotide

<400> SEQUENCE: 29
agcaucgagu cggccuuguu ggccuacugg                                    30

<210> SEQ ID NO 30
<211> LENGTH: 36
<212> TYPE: DNA

<213> ORGANISM: Artificial Sequence
<220> FEATURE:
<223> OTHER INFORMATION: Synthetic primer-linker
<220> FEATURE:
<221> NAME/KEY: misc_feature
<222> LOCATION: 27, 28, 29, 30, 31, 32, 33, 34, 35
<223> OTHER INFORMATION: n = A,T,C or G

<400> SEQUENCE: 30
gagagagaga gagcgactcg gatccannnn nnnnnc                             36

<210> SEQ ID NO 31
<211> LENGTH: 18
<212> TYPE: DNA
<213> ORGANISM: Artificial Sequence
<220> FEATURE:
<223> OTHER INFORMATION: Synthetic primer

<400> SEQUENCE: 31
agcatcgagt cggccttg                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic primer

<400> SEQUENCE: 32
gagagcgact cggatcca                                                 18

<210> SEQ ID NO 33
<211> LENGTH: 32
<212> TYPE: DNA
<213> ORGANISM: Artificial Sequence
<220> FEATURE:
<223> OTHER INFORMATION: Synthetic primer

<400> SEQUENCE: 33
ggacgagcgg ccgcgccttg ttggcctact gg                                 32

<210> SEQ ID NO 34
<211> LENGTH: 7
<212> TYPE: DNA
<213> ORGANISM: Artificial Sequence
<220> FEATURE:
<223> OTHER INFORMATION: Synthetic construct

<400> SEQUENCE: 34 aagatgc                                                              7

<210> SEQ ID NO 35
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 35
gtgcggcggc gtttaaacgg tcacctcgag                                    30

<210> SEQ ID NO 36
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 36
ctcgaggtga ccgtttaaac gcggccgcac                                30

<210> SEQ ID NO 37
<211> LENGTH: 33
<212> TYPE: DNA
<213> ORGANISM: Artificial Sequence
<220> FEATURE:
<223> OTHER INFORMATION: Synthetic primer-linker

<400> SEQUENCE: 37
gagatgaatt cctcgagctt tttttttttt ttt                            33

<210> SEQ ID NO 38
<211> LENGTH: 25
<212> TYPE: DNA
<213> ORGANISM: Artificial Sequence
<220> FEATURE:
<223> OTHER INFORMATION: Synthetic primer

<400> SEQUENCE: 38
aaacgctctg acttctcaca agatg                                     25

<210> SEQ ID NO 39
<211> LENGTH: 18
<212> TYPE: DNA
<213> ORGANISM: Artificial Sequence
<220> FEATURE:
<223> OTHER INFORMATION: Synthetic primer

<400> SEQUENCE: 39
gagatgaatt cctcgagc                                             18

<210> SEQ ID NO 40
<211> LENGTH: 18
<212> TYPE: DNA
<213> ORGANISM: Artificial Sequence
<220> FEATURE:
<223> OTHER INFORMATION: Synthetic primer

<400> SEQUENCE: 40
agatgctgga ctggagat                                             18

<210> SEQ ID NO 41
<211> LENGTH: 19
<212> TYPE: DNA
<213> ORGANISM: Artificial Sequence
<220> FEATURE:
<223> OTHER INFORMATION: Synthetic primer

<400> SEQUENCE: 41
gaatcaatta gcctctgga                                            19

<210> SEQ ID NO 42
<211> LENGTH: 21
<212> TYPE: DNA
<213> ORGANISM: Artificial Sequence
<220> FEATURE:
<223> OTHER INFORMATION: Synthetic primer

<400> SEQUENCE: 42
ggaaagaact tcactgaagt g                                         21

<210> SEQ ID NO 43

```
<211> LENGTH: 24
<212> TYPE: DNA
<213> ORGANISM: Artificial Sequence
<220> FEATURE:
<223> OTHER INFORMATION: Synthetic primer

<400> SEQUENCE: 43
ccatcagcct ctggaactgg agag                                              24

<210> SEQ ID NO 44
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: 3, 6, 9
<223> OTHER INFORMATION: n= I

<400> SEQUENCE: 44
acnrynhsng argmgaartc rgc                                               23

<210> SEQ ID NO 45
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: 6, 15, 21
<223> OTHER INFORMATION: n= I

<400> SEQUENCE: 45
ctrtcnadsg grswnccraa ncc                                               23
```

BONE POLYPEPTIDE-1

RELATED APPLICATION

This application is a 371 of PCT Application No. PCT/IB02/05778, filed Dec. 20, 2002, which claims the benefit of U.S. Provisional Application 60/341,224 filed Dec. 20, 2001, all documents are incorporated herein by reference.

BACKGROUND OF THE INVENTION a) Field of the invention

The present invention relates to a bone polypeptide and active fragments thereof. In particular, the present invention relates to bone polypeptide-1, active fragments thereof and nucleic acids encoding the same.

b) Brief Description of the Prior Art

Bone is a specialized connective tissue that is constantly remodelled by the reciprocal action of bone-forming cells (osteoblasts) and bone-resorbing cells (osteoclasts) (Manolagas, 2000). Full citations for the references cited herein are provided before the claims. In the developing organism, the skeletal system is formed either through endochondral or intramembranous ossification (Baron, 1999). Endochondral bone formation, exemplified by the development of the long bones of the limbs, involves replacement of a preformed cartilage template whereas intramembranous ossification, a process typical of flat bones of the skull, does not rely on an intermediate cartilaginous step. In both cases, osteoblasts originate from the mesenchyme and initially differentiate from the inner layer of the periosteum. Periosteal osteoblasts deposit lamellar bone, progressively becoming enthumbed in the matrix they deposit and finally differentiating into osteocytes. Osteocytes elaborate cytoplasmic extensions through canaliculi, thereby constituting a network of interconnected cells within bone tissue (Aarder et al., 1994). It is thought that this network senses load on the bones and alters bone activity according to the demands of that load.

Osteoporosis is characterized by a loss of bone mass due to an imbalance between bone resorption and bone formation. This degenerative disease affects 20 million women in the United States. Current treatment mainly involves the inhibition of the activity of osteoclasts by inhibitors such as bisphosphonates (Russell, 1999). Such anti-resorptive therapies slow down the progression of the disease but do not really help in rebuilding lost bone. Effective bone anabolics are thus needed. Unfortunately, with the possible exception of a fragment of parathyroid hormone ($PTH_{1-34}$; Neer et al., 2001), very few molecules have been shown to notably increase bone mass in osteoporotic patients. A number of growth factors and related molecules are now being considered as therapeutic agents. Insulin-like growth factor 1, (IGF1) is a protein that displays bone-sparing activity in the ovariectomized rat, a model of postmenopausal osteoporosis (Bagi et al., 1995). Basic fibroblast growth factor (bFGF) is another protein that was shown to enhance bone formation in vivo (Mayahara et al., 1993). However IGF1, as the name implies, is also an hypoglycemic factor and bFGF severely disrupts hematopoiesis. Hence, the in vivo specificity of these growth factors is difficult to ascertain and their clinical potential is unproven. There is thus a need to identify molecules that can efficiently and specifically increase bone formation.

Regulation of bone mass by the central nervous system has recently been reported by Ducy and colleagues (Ducy et al., 2000). These authors have shown that the ob/ob mice lacking a functional leptin gene have a higher bone mass. Leptin is a 16 kD hormone synthesized by the adipocytes and acting on hypothalamic neurons to regulate caloric intake (Unger, 2000). When injected intracerebroventricularly, leptin caused a loss of bone. It has been hypothesized that, in addition to adipocytes, osteoblasts per se might secrete a humoral factor that regulates bone mass through an hypothalamic relay. Thus, identification of such a factor might be useful to devise new therapies for the treatment of osteoporosis.

The inorganic component of bone is made up of hydroxyapatite crystals. Hence, in addition to its role as a supporting mechanical structure, the skeleton is a reservoir of calcium. Bone cells play a crucial role in the homeostasis of calcium and other ions such as phosphate. In particular, it has been proposed that bone cells secrete a hormone, tentatively called phosphatonin, that regulates phosphate retention by kidney tubules. It has been reported that phosphatonin levels are elevated in conditioned medium of tumor cells derived from a rare disease called oncogenic hypophosphatemia osteomalacia (Kumar, 2000). Furthermore, it has been postulated that phosphatonin is a substrate for Phex, a metallopeptidase found at the cell surface of osteoblasts and osteocytes (Frota Ruchon et al., 2000). This hypothesis is supported by the fact that patients with X-linked hypophosphatemia harbor deleterious mutations in the Phex coding sequence (The Hyp consortium, 1995) and presumably have elevated levels of active phosphatonin. Low serum phosphate levels are associated with impaired bone quality. Hypophosphatemia could be remedied by injection of phosphatonin antagonists. In view of the above, it is clear that there is a need to identify the molecular nature of phosphatonin or other molecules that regulate phosphate metabolism. In particular, there is a tremendous need to identify bone polypeptides that may be useful as therapeutic agents.

SUMMARY OF THE INVENTION

In order to meet these needs, the present invention is directed to recombinant bone polypeptide-1 (BP-1), proteins sharing substantial homology to BP-1 and active fragments thereof. Bone polypeptide-1 is polypeptide expressed in bone. Bone polypeptide 1 can be synthesized chemically, recombinantly produced, isolated and/or purified from a recombinant host or it and it can be isolated and/or purified from its natural source. Sources of bone polypeptide-1 include all organisms containing bone since bone polypeptide-1 is predominantly expressed in bone cells. Preferred sources of bone polypeptide 1 include rat, mouse, python, cow and chicken. An especially preferred source of bone polypeptide-1 is a human.

The present invention is further directed to nucleic acids encoding bone polypeptide-1 and active fragments thereof; a vector containing the nucleic acids and a host cell carrying the vector. The present invention is further directed to processes to produce bone polypeptide-1 and active fragments thereof, processes to produce cells capable of producing the bone polypeptide-1 and active fragments thereof and to produce a vector containing DNA or RNA encoding bone polypeptide-1 and active fragments thereof. The present invention is further directed to methods for treating bone and renal diseases and methods for using pharmacologic compositions comprising an effective amount of bone polypeptide-1 and active fragments thereof. The invention also encompasses monoclonal and polyclonal antibodies specifically recognizing bone polypeptide-1 and active fragments thereof.

The present invention is further directed to an isolated nucleic acid encoding bone polypeptide-1 and active fragments thereof. The nucleic acid may be isolated from an animal, preferably a human. Other sources of the nucleic acid include rats, cows, snakes, mice and chickens.

Bone polypeptide-1 may regulate bone cell proliferation and/or bone cell differentiation and/or osteoblast activity via an autocrine, paracrine or endocrine pathway. Active fragments of bone polypeptide-1 are fragments that have similar activity as the full length protein and therefore may regulate bone cell proliferation and/or bone cell differentiation and/or osteoblast activity via an autocrine, paracrine or endocrine pathway.

The present invention is further directed to nucleic acids having sequences selected from: SEQ ID NO: 2; SEQ ID NO: 3; SEQ ID NO: 4; SEQ ID NO: 5; SEQ ID NO: 6, SEQ ID NO: 7 and homologous sequences.

The present invention is further directed to vector including a nucleic acid encoding bone polypeptide-1 and active fragments thereof. In one format, the vector includes an expression control sequence operably linked to the nucleic acid. The expression control sequence may be a promoter such as a prokaryotic promoter or a eukaryotic promoter. The vector may be present in an isolated cell such as a prokaryotic cell or a eukaryotic cell.

The present invention is further directed to a method of producing bone polypeptide-1 or active fragments thereof by culturing a cell containing an vector containing a nucleic acid encoding bone polypeptide-1 under conditions permitting expression of the polypeptide and purifying the polypeptide from the cell or culture medium of the cell. The cell may be a prokaryotic cell or a eukaryotic cell.

The present invention is further directed to an isolated nucleic acid that hybridizes under high stringency conditions to a nucleic acid including nucleotide sequences such as SEQ ID NO: 2; SEQ ID NO: 3; SEQ ID NO: 4; SEQ ID NO: 5; SEQ ID NO: 6, SEQ ID NO: 7, SEQ ID NO: 8, and the complements thereof wherein the high stringency conditions includes hybridizing in 0.15 M NaCl at 72° C. for about 15 minutes and washing the hybridized DNA in 0.2×SSC at 65° C. for 15 minutes. The nucleic acid may be isolated from an animal, preferably a human. Other sources of the nucleic acid include rats, cows, snakes, mice and chickens.

The nucleic acids of the invention may be cloned into an vector. The vector may further include an expression control sequence operably linked to the nucleic acid. The expression control sequence may be a promoter such as a prokaryotic promoter or a eukaryotic promoter.

The present invention is further directed to isolated and/or purified and/or recombinant bone polypeptide-1 or an active fragment thereof in a pharmaceutical composition. The polypeptide may be isolated and/or purified from a human. Alternatively, the polypeptide may be recombinantly produced from the nucleic acid encoding the human polypeptide. The polypeptide may also be isolated from rat, cow, snake, mouse or chicken. Alternatively, the polypeptide may be recombinantly produced from the nucleic acid encoding the rat, cow, snake, mouse or chicken polypeptide.

The present invention is further directed to polypeptides having amino acid sequences selected from of SEQ ID NO: 9; SEQ ID NO: 10; SEQ ID NO: 11; SEQ ID NO: 12; SEQ ID NO: 13; SEQ ID NO: 14, SEQ ID NO: 20, SEQ ID NO: 21 SEQ ID NO: 22; SEQ ID NO: 23; SEQ ID NO: 24; SEQ ID NO: 25; SEQ ID NO: 26, SEQ ID NO: 27, and SEQ ID NO: 28.

The present invention is further directed to an expression vector containing a coding sequence the sequence of which encodes bone polypeptide-1 or an active fragment thereof, the vector being suitable for genetic therapy.

The present invention is further directed to a method to deliver a nucleic acid, the sequence of which encodes bone polypeptide-1 or a fragment thereof, into a host for therapy. In one format of the method of the invention, the delivery is by adenovirus.

The present invention is further directed to a method of treating a bone disorder or osteoporosis comprising administering an effective amount of bone polypeptide-1 or a fragment thereof.

BRIEF DESCRIPTION OF THE DRAWINGS

FIGS. 1A, B show the results of a Northern analysis comparing the expression of a mouse cDNA encoding bone polypeptide-1 (BP-1) in a variety of embryonic and adult mouse tissues. A. Five micrograms of total RNA was loaded in lanes 1 to 16. 1, brain e11.5; 2, adult brain; 3, gonads e14.5; 4, adult testis; 5, heart e12.5; 6, adult heart; 7, intestine e14.5; 8, adult intestine; 9, kidney e13.5; 10, adult kidney; 11, liver e11.5; 12, adult liver; 13, lung e12.5; 14, adult lung; 15, spleen e15.5; 16, adult spleen. B. One and a half microgram of polyA(+) RNA was loaded in lanes 21 to 23. 21, calvaria e15.5; 22, adult kidney; 23, adult liver. Bars indicate migration of 28S and 18S ribosomal RNA.

FIG. 2 shows the nucleotide sequence of a full length mouse cDNA encoding bone protein-1 (SEQ ID NO:1). The open reading frame is written in capital letters, the polyadenylation signal is in bold characters, the sequence corresponding to the original ca155-cap1-c2-neg306 clone is underlined.

FIGS. 3A-F show brightfield (A,D) and darkfield (B,C,E, F) images of sections through the limb of a mouse embryo at 16 days of gestation (A-C) or through the head of a mouse embryo at 13 days of gestation (D-F) hybridized with a probe complementary to a novel cDNA encoding bone polypeptide-1 (B,E) or to Cbfa1, a transcription factor expressed mainly in the osteoblast lineage (C,F).

FIG. 4 shows an alignment of the coding sequences from human (*Homo sapiens*) (SEQ ID NO:2), mouse (*Mus musculus*) (SEQ ID NO:3), rat (*Rattus norvegicus*) (SEQ ID NO:4), bovine (*Bos taurus*) (SEQ ID NO:5), chicken (*Gallus gallus*) (SEQ ID NO:6), and python (*Python molurus bivittatus*) (SEQ ID NO: 7) BP-1 cDNAs. The consensus DNA sequence for BP-1 is provided as SEQ ID NO: 8.

FIG. 5A shows an alignment of the primary sequences of BP deduced from cDNAs isolated from tissues of the human (*Homo sapiens*) (SEQ ID NO:9), mouse (*Mus musculus*) (SEQ ID NO:10), rat (*Rattus norvegicus*) (SEQ ID NO:11), bovine (*Bos taurus*) (SEQ ID NO:12), chicken (*Gallus gallus*) (SEQ ID NO:13) and python (*Python molurus biviffatus*) (SEQ ID NO:14). The consensus polypeptide sequence for BP-1 is provided as SEQ ID NO: 15. Sequence of the putative signal peptides are underlined. Putative processing sites are boxed.

FIG. 5B shows an alignment of a region of homology between BP-1 and members of the natriuretic peptides family. Numbering of amino acids is according to the full length precursor protein (SEQ ID NO:9 for BP-1). The human sequence is SEQ ID NO: 16. The rat atrial natriuretic factor protein region is SEQ ID NO: 17. The rat brain natriuretic factor protein region is SEQ ID NO: 18. The rat C-type natriuretic factor protein region is SEQ ID NO: 19.

FIG. 7A depicts an expression vector for BP-1 (plasmid GD46) that can be used to generate cell lines secreting the BP-1 polypeptide or fragments thereof in the culture medium. The vector comprises components of a transcription unit for mouse BP-1 (700, 701, 702) as well as a transcription unit to confer resistance to puromycin (703).

FIG. 7B shows the standard curve of an enzyme-linked immunoadsorbent assay (ELISA) performed on increasing quantities of synthetic peptide derived from the C terminal region of BP-1.

FIG. 9A depicts a vector (plasmid GD28b) that can be used to generate recombinant adenoviral particles expressing BP-1 coding sequence. The vector comprises a transcription unit for mouse BP-1 (901) flanked by two regions of the adenovirus serotype 5 genome (902, 903).

FIG. 9B shows the result of an ELISA to detect BP-1 products in the medium of primary cultures of rat osteoblasts infected with recombinant adenoviral particles at day 11 of culture.

DETAILED DESCRIPTION OF THE INVENTION

A) Definitions

Figure 6A:
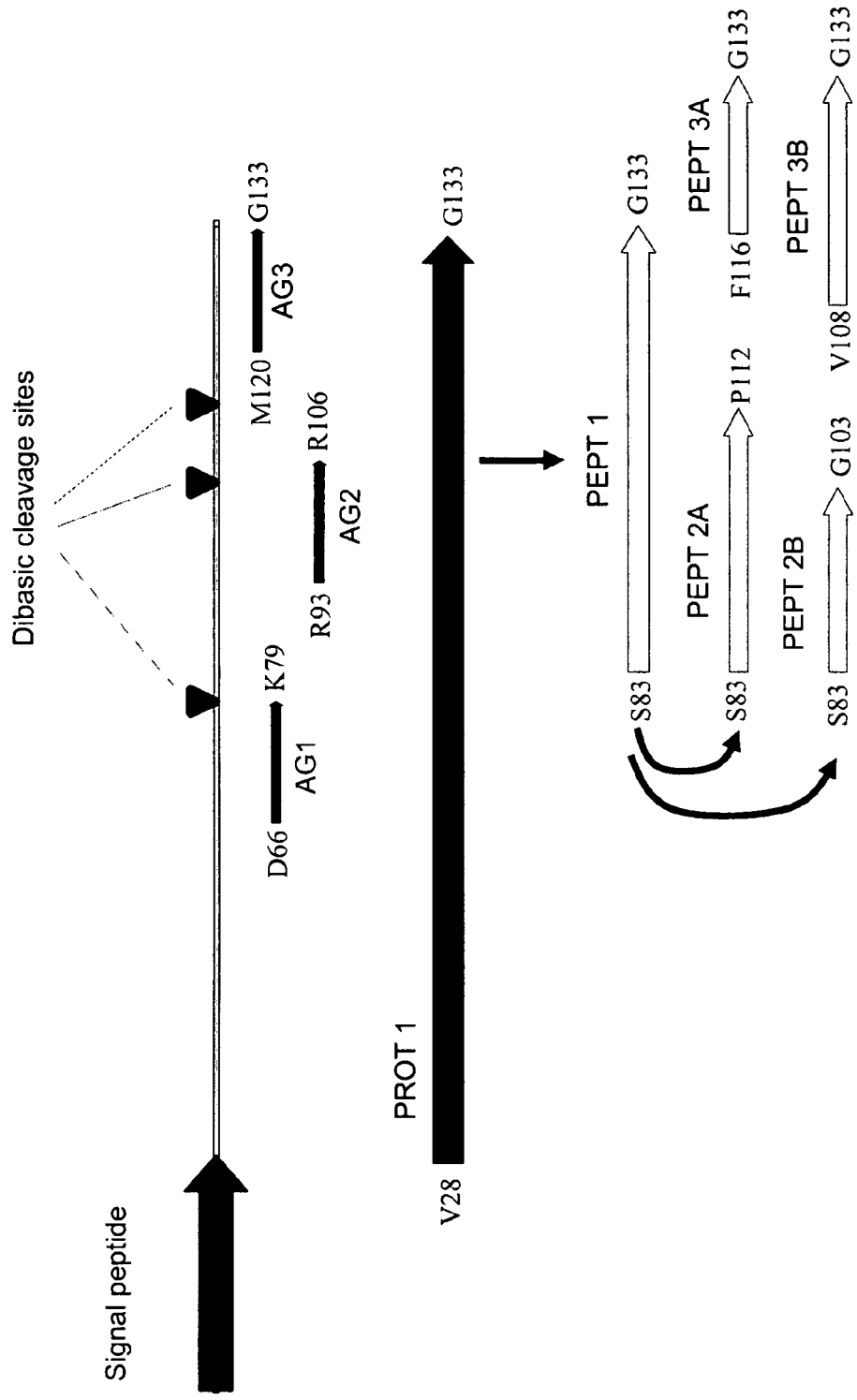
FIG. 6A depicts the full length protein derived from the human BP-1 cDNA (SEQ ID NO: 2) and is presented as SEQ ID NO: 9. The signal peptide and corresponding signal peptidase cleavage site are shown. Also shown are the conserved dibasic cleavage sites, the putative products generated by processing of the protein (PROT 1 (SEQ ID NO: 20), PEPT 1 (SEQ ID NO: 21), PEPT 2A (SEQ ID NO: 22), PEPT 3A (SEQ ID NO: 23), PEPT 2B (SEQ ID NO: 24), PEPT 3B (SEQ ID NO: 25)), and the position of synthetic peptides used to raise antibodies (AG1 (SEQ ID NO: 26), AG2 (SEQ ID NO: 27), AG3 (SEQ ID NO: 28)). The residues at the N and C termini of peptides are indicated and numbered according to the initiator methionine of SEQ ID NO:9.

Throughout the text, the word "kilobase" is generally abbreviated as "kb", the words "deoxyribonucleic acid" as "DNA", the words "ribonucleic acid" as "RNA", the words "complementary DNA" as "cDNA", the words "polymerase chain reaction" as "PCR", the words "expressed sequenced tag" as "EST", and the words "reverse transcription" as "RT". Nucleotide sequences are written in the 5' to 3' orientation unless stated otherwise. Amino acid sequences are written from the N terminus unless stated otherwise.

In order to provide an even clearer and more consistent understanding of the specification and the claims, including the scope given herein to such terms, the following definitions are provided:

Exogenous nucleic acid: A nucleic acid (such as cDNA, cDNA fragments, genomic DNA fragments, mRNA fragments, antisense RNA, oligonucleotide) which is not naturally part of another nucleic acid molecule. The "exogenous nucleic acid" may be from any organism, purely synthetic, or any combination thereof.

Expressed sequenced tag: sequence information on a small nucleic acid (typically 200-500 bp) derived from a gene transcript.

Hormone: a molecule, generally polypeptidic in nature, secreted extracellularly by one cell type to modulate the activity of target cells.

Hormone precursor. Refers to a secreted protein that is processed in the secretory pathway such that one or more fragments are released extracellularly. Fragments can be further modified (e.g. amidation at the C terminus) before or after release in the extracellular space.

Host: A cell, tissue, organ or organism capable of providing cellular components for allowing the expression of an exogenous nucleic acid. The exogenous nucleic acid maybe cloned into a vector. This term is intended to also include hosts which have been modified in order to accomplish these functions. Bacteria, fungi, animal (cells, tissues, or organisms) and plant (cells, tissues, or organisms) are examples of a host.

Insertion: The process by which a nucleic acid is introduced into another nucleic acid. Methods for inserting a nucleic acid into another normally requires the use of restriction enzymes and such methods of insertion are well known in the art.

In silico: using computer and bioinformatics software and hardware.

Nucleic acid: Any DNA, RNA sequence or molecule having one nucleotide or more, including nucleotide sequences encoding a complete gene. The term is intended to encompass all nucleic acids whether occurring naturally or non-naturally in a particular cell, tissue or organism. This includes DNA and fragments thereof, RNA and fragments thereof, cDNAs and fragments thereof, expressed sequence tags, artificial sequences including randomized artificial sequences.

Open reading frame ("ORF"). The portion of a cDNA that is translated into a protein. Typically, an open reading frame starts with an initiator ATG codon and ends with a termination codon (TAA, TAG or TGA).

Protein products: refers to the various peptides or polypeptides generated after translation of a single mRNA. Polypeptides refer to amino acids linked to form a peptide or a full length protein.

Recombinant: The term "recombinant" in association with "vector" refers to a vector which has been modified to contain a non-native exogenous nucleic acid.

Secreted protein: any protein that enters the cellular secretory pathway. Typically, secreted proteins are synthesized bearing a signal peptide which is removed shortly after its synthesis.

Signal peptide: a peptide capable of directing a nascent protein to the cell secretory pathway. It is generally accepted that a signal peptide is composed of an initiating methionine, a highly hydrophobic stretch, typically 10 to 15 residues long, and a signal peptidase cleavage site.

Transcription unit: As used herein, a "transcription unit" refers to a nucleic acid which comprises an enhancer sequence, a promoter sequence, and a transcription termination sequence, all operably linked together. Preferably, the enhancer and promoter sequences are constitutively active in various hosts. Enhancer and promoter sequences can be derived for example from the cytomegalovirus (CMV) immediate-early genes or from the Rous sarcoma virus (RSV) long terminal repeat. Preferably, the transcription unit is comprised within a vector.

Transfection: the process of introducing nucleic acids in eukaryotic cells by any means such as electroporation, lipofection, precipitate uptake, micro-injection. A cell having incorporated an exogenous nucleic acid is said to be transfected.

Vector: A RNA or DNA molecule which can be used to transfer an RNA or DNA segment from one organism to another. Vectors are particularly useful for manipulating genetic constructs and different vectors may have properties particularly appropriate to express protein(s) in a recipient during cloning procedures and may comprise different selectable markers. Bacterial plasmids are commonly used vectors.

B) General Overview of the Invention

The invention is based on isolated nucleic acids encoding bone polypeptide-1. The invention encompasses isolated or substantially purified nucleic acid or protein compositions. In the context of the present invention, an "isolated" or "substantially purified" DNA molecule or an "isolated" or "substantially purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. An isolated or purified DNA or polypeptide may be synthesized chemically, may be produced using recombinant DNA techniques and then isolated or purified or may be isolated or purified from its natural host. An "isolated" or "substantially purified" nucleic acid molecule or protein, or biologically active portion thereof, is substantially free of other cellular material, or culture medium when produced by recombinant techniques and, in some circumstances, further purifed, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals.

i) Cloning of a cDNA Fragment Encoding Bone Polypetide-1

We have previously developed a screening system that allows the rapid identification of nucleic acids encoding signal peptides from complex libraries of cDNA fragments (International patent application No. PCT/CA01/01169; U.S. patent application Ser. No. 09/641,931). A library enriched in 5' fragments of cDNAs derived from developing calvaria was obtained using the so-called "oligo-capping" method (Maruyama and Sugano, 1994). Briefly, the top halves of skulls of e15.5 mouse embryos were dissected free from nervous or skin tissue. Total RNA was extracted using the guanidium/phenol method and mRNA was isolated using Oligotex mRNA kit (Qiagen, Mississauga, Canada). A synthetic oligoribonucleotide (RNA30-1; 5'-agcaucgagucggc-cuuguuggccuacugg-3') SEQ ID NO:29 was specifically ligated to the 5' extremities of mRNAs whose CAP moiety had been converted to a free phosphate group by the action of tobacco acid pyrophosphatase. The first strand of corresponding cDNA was synthesized using a primer-linker comprising a random sequence of 9 nucleotides (36-2V; 5'-gagagagagagagcgactcggatccannnnnnnnnc-3') SEQ ID NO 30. The resulting first strand cDNA was amplified by 30 cycles of PCR using primers complementary to both extremities (18-114V; 5'-agcatcgagtcggccttg-3') SEQ ID NO: 31 and (18-99V; 5'-gagagcgactcggatcca-3') SEQ ID NO: 32. Amplicons were purified and subjected to a further 10 cycles of semi-nested PCR using primers 18-99V and 32-4V (5'-ggac-gagcggccgcgccttgttggcctactgg-3') SEQ ID NO:33. PCR products were digested with NotI and BamHI, size-selected by electrophoresis (500-1200 bp) and directionally cloned in an expression/screening vector digested with NotI and BamHI. The library numbered approximately 3,000,000 primary clones. Sequencing of randomly chosen inserts revealed that the average insert size was 575 bp and that 60% of inserts corresponded to 5' fragments of cDNAs. The library was expression screened in BHK-21 fibroblasts. Selected fragments were amplified, cloned in the pBluescript KS II+ vector and sequenced using a CEQ2000™ automated sequencer.

One of the retrieved fragments (ca155-cap1-c2-neg306, 433 bp in length) encoded a putative translation product of 124 residues containing a signal peptide. Interestingly, this translation product harbored sequences reminiscent of dibasic cleavage sites found in peptide hormone precursor (KKKR (SEQ ID NO: 132) at position 76-79 and KKR at position 110-112). This observation prompted us to determine the expression profile of the corresponding gene by Northern analysis of RNA extracted from 52 different tissues and cell lines. No signal was detected after an exposure of 7 days; a representative autoradiograph is shown in FIG. 1A. In order to verify that the retrieved fragment derived from a cellular transcript, Northern analysis was performed with 1.5 μg of polyA+RNA extracted from e15.5 mouse calvaria, adult liver and adult kidney (FIG. 1B). A clear signal (arrow; 25), corresponding to a mRNA of approximately 1.3 kb, was specifically detected in the embryonic calvaria. Taken together, these results indicate that ca155-cap1-c2-neg306 is derived from a mRNA that encodes a bone protein that is specifically expressed in bone tissue.

ii) Results from Database Mining; Cloning of Full Length Mouse cDNA Containing c155-cap1-c2-neg306

Because of the interesting features of clone ca155-cap1-c2-neg306, we carried out extensive database searches to compare its sequence with those deposited in the public domain. We used the standard Blastn tool (v2.2.4, Aug. 26, 2002) with the following parameter set: expect value of 10, low complexity filter. There was only one significant match to an entry (accession XM_155941.1) in the non redundant (nr) set of the Genbank™ database. This clone (designated LOC239790) encodes a putative protein whose N terminal sequence is identical to that of ca155-cap1-c2-neg306 but diverges at residues Gln$^{102}$. Searches in dbEST revealed that ca155-cap1-c2-neg306 shows high homology to a bovine EST (77.5% homology, accession number BF045261), to an uncharacterized mouse EST (accession number BB638598.1), to 3 human ESTs from metastatic chondrosarcoma (accession numbers BQ021661, BQ001512, BQ000995) and that the last 102 nucleotides of ca155-cap1-c2-neg306 shows high homology (85.8%) to the last 105 nucleotides of a rat EST (accession number Al178209). It should be noted that a valid ORF can not be deduced from the cDNA sequences of either mouse, rat or human ESTs. The 526 bp bovine EST contained an ORF of 132 residues. In silico assembly of ca155-cap1-c2-neg306 and the rat EST yielded a 0.99 kb chimeric sequence, roughly corresponding to the size of the expected full length transcript minus polyA tail (see Northern analysis, FIG. 1B).

Since we had initially cloned the 5' end of ca155-cap1-c2-neg306, we used a modified 3' RACE strategy to obtain a full length cDNA (see Materials and Methods in the Examples section). Sequences from at least five different clones were aligned together with ca155-cap1-c2-neg306 to reconstitute the full length consensus cDNA sequence shown on FIG. 2. The 1280 bp cDNA (SEQ ID NO:1) contains an ORF of 393 bp (uppercase) flanked by 61 bp and 811 bp of untranslated sequences at the 5' and 3' ends, respectively (lowercase). A polyadenylation signal is found 14 bp upstream of a polyA stretch. The putative initiator ATG codon is found in an adequate Kozak context (AAGATGC, SEQ ID NO: 25).

iii) Expression Profiling on Histological Sections of Mouse Embryos

To determine which bone cells express the cDNA from which ca155-cap1-c2-neg306 derives, in situ hybridization was performed on sections of e13.5 and e16.5 mouse embryos using standard procedures. Consecutive sections were hybridized with a probe partially complementary to Cbfa1 transcripts. Cbfa1 is a transcription factor expressed in cells of the osteoblast lineage and whose activity is essential for proper development of the skeleton (Ducy, 2000). As shown in FIG. 3B, the ca155-cap1-c2-neg306 probe specifically labels cells surrounding the bone collar in e16.5 limbs. These cells are located in the periosteum and are cells of the osteoblast lineage. This is revealed by the fact that they express Cbfa1 (FIG. 3C). At e13.5, expression of ca155-cap1-c2-neg306 is seen in a few cells in the vicinity of cartilaginous formations in the skull (FIG. 3E). These cells are also labeled by the Cbfa1 probe (FIG. 3F). Thus, the cDNA from which ca155-cap1-c2-neg306 derives is expressed in cells of the osteoblast lineage.

iv) Cloning of Vertebrate Homologs

Because of its features, the cDNA from which ca155-cap1-c2-neg306 derives will be referred hereafter as mouse BP-1, mouse bone polypeptide-1. As discussed in more detail below, various homologs, including at least one human homolog to BP-1 exist. Bone polypeptide-1, as defined herein, refers to a polypeptide expressed in bone. As discussed in more detail below, bone polypeptide-1 may regulate bone cell proliferation and/or bone cell differentiation and/or osteoblast activity via an autocrine, paracrine or endocrine pathway.

BP-1 DNA Sequences

The BP-1 DNA used in any embodiment of this invention can be BP-1 cDNA obtained as described herein, or alternatively, can be any oligonucleotide sequence having all or a portion of a sequence represented herein, or their functional equivalents. Such oligodeoxynucleotide sequences can be produced chemically or mechanically, using known techniques.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length BP-1 cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. 1988; Higgins et al. 1989; Corpet et al. 1988; Huang et al. 1992; and Pearson et al. 1994. The ALIGN program is based on the algorithm of Myers and Miller, supra. The BLAST programs of Altschul et al., 1990, are based on the algorithm of Karlin and Altschul supra.

Software for performing BLAST analyses is publicly available through the web site for National Center for Biotechnology Information (NCBI). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See the NCBI web site. Alignment may also be performed manually by inspection.

For purposes of the present invention, comparison of BP-1 nucleotide sequences for determination of percent sequence identity to the BP-1 sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two BP-1 nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a BP-1 polynucleotide comprises a sequence that has at least 60%, 61%, 62%, 63%, 64%, 65%, 66%, 67%, 68%, 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a BP-1 peptide indicates that a peptide comprises a sequence with at least 60%, 61%, 62%, 63%, 64%, 65%, 66%, 67%, 68%, 69%, 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two BP-1 nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984; $T_m$ 81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1× SSC, 0.1% SDS at 65° C.

Protein Sequences

The present invention includes peptides which are derivable from BP-1. A peptide is said to be "derivable from a naturally occurring BP-1 amino acid sequence" if it can be obtained by fragmenting a naturally occurring sequence, or if it can be synthesized based upon a knowledge of the sequence of the naturally occurring BP-1 amino acid sequence or of the genetic material (DNA or RNA) which encodes this sequence.

Included within the scope of the present invention are those molecules which can be said to be "derivatives" or "active fragments" of BP-1 referred herein as "BP-1 products". Such a "derivative" or "active fragment" has one or more of the following characteristics: (1) it shares substantial homology with BP-1 or a similarly sized fragment of BP-1; (2) it is capable of functioning as a bone hormone and (3) using at least one of the assays provided herein, the derivative has either (i) a bone hormone activity, or, (ii) an activity on the kidney. Bone hormone activity refers to an ability to regulate bone cell proliferation and/or bone cell differentiation and/or of osteoblast activity, via an autocrine, paracrine or endocrine pathways.

A derivative of BP-1 is said to share "substantial homology" with BP-1 if the amino acid sequences of the derivative is at least 60%, and more preferably at least 80%, and most preferably at least 90%, the same as that of BP-1.

The derivatives of the present invention include BP-1 fragments which, in addition to containing a sequence that is substantially homologous to that of a naturally occurring BP-1 peptide may contain one or more additional amino acids at their amino and/or their carboxy termini. Thus, the invention pertains to polypeptide fragments of BP-1 that may contain one or more amino acids that may not be present in a naturally occurring BP-1 sequence. The additional amino acids may be D-amino acids or L-amino acids or combinations thereof. Furthermore, the additional amino acids may be naturally occurring amino acids or non-naturally occurring amino acids such as L-tert-leucine; L-homophenylalanine; D-homophenylalanine; D-methionine; Halogenated D and L-phenylalanines, tyrosines, and tryptophans; D-2-aminopimelic acid and L-2-aminopimelic acid The invention also includes BP-1 fragments which, although containing a sequence that is substantially homologous to that of a naturally occurring BP-1 peptide may lack one or more additional amino acids at their amino and/or their carboxy termini that are naturally found on a BP-1 peptide. Thus, the invention pertains to polypeptide fragments of BP-1 that may lack one or more amino acids that are normally present in a naturally occurring BP-1.

The invention also encompasses the obvious or trivial variants of the above-described fragments which have inconsequential amino acid substitutions (and thus have amino acid sequences which differ from that of the natural sequence) provided that such variants have a bone hormone activity which is substantially identical to that of the above-described BP-1 derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

Bone Polypeptide-1 Homologs

A cDNA encoding BP-1, or a portion thereof can be used to identify similar sequences in other vertebrate species and thus, to identify or "pull out" sequences which have sufficient homology to hybridize to BP-1 cDNA or mRNA or a portion thereof under conditions of low stringency. Those sequences which have sufficient homology (generally greater than 40%) can be selected for further assessment using the method described herein. Alternatively, high stringency conditions can be used as discussed above. In this manner, DNA of the present invention can be used to identify, in other species, sequences encoding polypeptides having amino acid sequences similar to that of BP-1 and thus to identify bone polypeptides in other species. Thus, the present invention includes not only BP-1, but also related proteins encoded by DNA which hybridizes, preferably under high stringency conditions, to DNA of the present invention.

BLAST searches of the mouse BP-1 sequence using the Ensembl web site (containing the sequence of the human genome, v8.30a.1, August 2002 data) revealed that a human homolog of BP-1 might exist. Indeed, homologous sequences are found on human chromosome 3q28 in contigs AC019234.5.48926.64909 (nt 12659-12937, 75% homology), AC019234.5.130697.209258 (nt 75405-75529, 79% homology), AC019234.5.89412.130596 (nt 39498-39560, 92% homology). The Genescan algorithm predicts 4 exons but those are disordered and not annotated as part of a single gene and, furthermore, the predicted translation product do not match the primary sequence of BP-1, presumably because Genescan has not identified the correct ORF. Thus, the ORF predicted from the BP-1 cDNA (FIG. 2) can not be determined solely by in silico analysis of the sequence of the human genome. Therefore, in order to clone a human homolog of BP-1, we performed RT-PCR on human bone marrow mRNA using two primers encompassing the putative initiator and termination codons found in the human genome sequence. In addition, the rat homolog of BP was cloned by low-stringency RT-PCR using one primer encompassing the putative initiator codon and another encompassing a region in the 3' untranslated region of the mouse cDNA. To identify evolutionarily conserved domains within the BP-1 protein, we obtained sequence information on BP-1 from non mammalian species. The cDNA encoding chicken (*Gallus gallus*) BP-1 was retrieved by 'BLASTing' the human ORF against the BBSRC Chicken EST Project database (Blastn tool, all tissues, matrix BLOSUM62, expectation $10^{-2}$). A portion of the cDNA encoding snake (*Python molurus bivittatus*) BP-1 was cloned by RT-PCR using degenerate oligonucleotide primers and starting from RNA extracted from the vertebrae of a young python (See Materials and Methods in the Examples section.) FIG. 4 shows the alignment of the nucleic acid sequences encoding human, bovine, mouse, rat, chicken, and python BP-1. Allelic variations of the nucleic acid sequences described herein are also encompassed in the invention.

FIG. 5A shows the alignment of the ORFs derived from the BP-1 cDNAs of mouse, human, rat, cow, chicken. The partial ORF deduced from the python sequence is also aligned. The presence of a cleavable signal peptide as well as the position of the putative processing sites are conserved across species (respectively underlined and boxed in FIG. 5A). In silico analysis indicates that a) the region of the protein that lies between the 2 dibasic cleavage sites (residues 83-112 in the human sequence) is well conserved (overall identity of 60%, overall similarity of 76%); b) the C terminal region of the protein (residues 116-133 in the human sequence) is also well conserved (human and mouse share 94.4% similarity and identity; human and chicken share 83.3% similarity and 61.1% identity). The observation that the dibasic cleavage sites are found in various species suggests that BP-1 is a prohormone precursor conserved in terrestrial vertebrates. Furthermore, analysis of the conserved domains suggests that the bioactive protein products derive from the C terminal half of BP-1.

In silico analysis indicates that full length human BP-1 has the following feature: it has a molecular weight of 14,832 g/mol and an isoelectric point of 9.62; it contains neither N-glycosylation sites nor disulfide bridges. Despite extensive searches in public databases (e.g. InterPro, ProDom, STN DGENE), BP-1 shows no significant homology to any known protein, protein motif or protein domain. We have found however that residues 116-124 of BP-1 (numbering from the human sequence) show some homology to members of the natriuretic peptides family. FIG. 5B shows the alignment of the homologous regions between BP-1 and natriuretic peptides. The 2 cysteine residues conserved in all natriuretic peptides form an intramolecular disulfide bridge essential for their bioactivity (Inagami et al., 1985). Cysteine residues involved in cyclization are not found in BP-1. Interestingly however, it has been reported that a synthetic 'linear' analog of the atrial natriuretic peptide could displace the binding of atrial natriuretic factor to its receptor but failed to activate synthesis of second messengers (Olins et al., 1988). Thus, it is possible that a BP-1 protein product could be related both biochemically and functionally to the natriuretic peptides.

v) Production of Antibodies Against Portions of BP-1.

In order to detect the BP-1 protein products, antibodies were raised against synthetic peptides derived from 3 regions of the full length protein AG-1: (DELVSLENDVIETK (SEQ ID NO:26), AG-2: (RLSAGSVDHKGKQR) SEQ ID NO: 27, and AG-3: (MDRIGRNRLSNSRG) SEQ ID NO: 28). The chosen regions have a high antigenicity index as predicted by the algorithm of Hopp and Woods (Hopp and Woods, 1981). The positions of the antigenic peptides are indicated on the model of human BP-1 shown on FIG. 6A. To increase immunogenicity, antigenic peptides comprise a N- or C-terminal cysteine to allow covalent coupling to a carrier protein (e.g. keyhole limpet hemocyanin, bovine serum albumin). The peptide/carrier complex are injected subcutaneously into animals (e.g. rabbits) and antisera are obtained using standard protocols. (See Materials and Methods in Examples section.) Affinity chromatography was used to purifiy the fraction of immunoglobulins specific to the peptide used to elicit an immune response.

Both monoclonal and polyclonal antibodies are included within the scope of this invention as they can be produced by well established procedures known to those of skill in the art. Additionally, any secondary antibodies, either monoclonal or polyclonal, directed to the first antibodies would also be included within the scope of this invention.

BP-1 is Secreted Extracellularly and Can be Processed

Figure 6B:
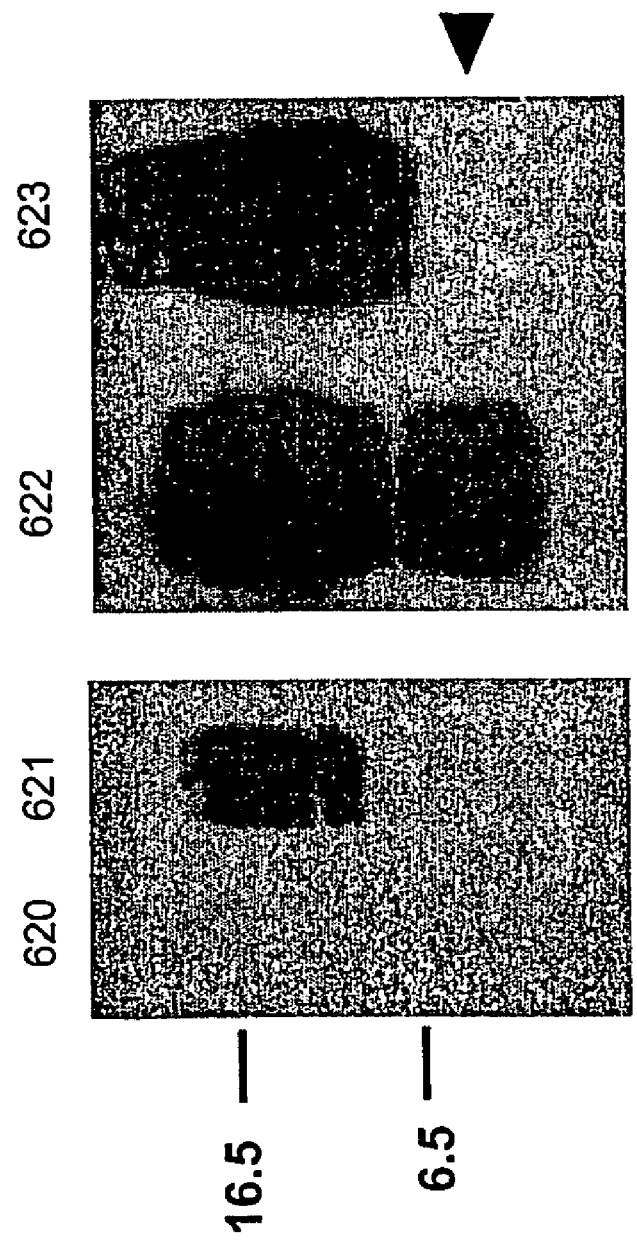
FIG. 6B shows a picture of Western analysis on cell extracts (lanes 620) or precipitated medium (lanes 621) from cells transfected with a vector expressing wild type BP-1 mouse cDNA (lanes 620, 621, 622), or a form of BP-1 mouse cDNA where one of the dibasic cleavage site was mutated (lanes 623). Migration of molecular weight markers is indicated.

To begin assessing the biochemical and biological properties of BP-1, a cDNA encoding the mouse protein was inserted into a mammalian expression vector and this vector was transfected in HEK293A cells. Immunofluorescence analysis after cell permeabilization showed that BP-1 is mainly localized to the Golgi apparatus and in small cytoplasmic vesicles of transfected cells. No signal was detected at the cell surface. Western analysis of cell lysates and culture medium using antibodies raised against the C terminal region of human BP-1 (AG3) (SEQ ID NO: 28) revealed that the bulk of the protein products is secreted in the culture medium (FIG. 6B, compare lanes 620 and 621). The major secreted form has an apparent molecular weight of 13 kD, presumably corresponding to the BP-1 precursor after removal of the signal peptide. Upon longer exposure (FIG. 6B, lane 622), a smaller product with an apparent molecular weight of ~6 kD is reproducibly found in the culture medium of transfected HEK293A cells. This ~6 kD band is absent when cells are transfected with a vector expressing a form of the mouse cDNA where the dibasic cleavage site at position 76-79 is mutated (KKKR (SEQ ID NO: 132)->AS, FIG. 6B, lane 623).

Given these results, we predict that BP-1 is processed according to the following scheme. After translocation in the endoplasmic reticulum, the signal peptide is cleaved and the protein (PROT 1, SEQ ID NO: 20) may be further processed in the secretory pathway or extracellular space to yield bioactive products. Candidate processing enzymes include furin (Denault and Leduc, 1996; GenBank™ PID accession number g31478), a related convertase or, as discussed below, corin (GenBank™ PID accession number g5729989). Our results indicate that the BP-1 precursor may be cleaved at arginine[82] (numbering according to human sequence) in an heterologous expression system (e.g. HEK293A fibroblasts) to generate PEPT 1 (SEQ ID NO: 21). Additional processing may occur C terminal to arginine[115] at a typical dibasic site to generate PEPT 2A (SEQ ID NO: 22) and PEPT 3A (SEQ ID NO: 23). Alternative processing may occur at a basic residue (lysine[104]) upstream of the second dibasic site by an atypical convertase, similar to what has been reported for the processing of a natriuretic peptide precursor by the corin protease (Yan et al., 2000; Yan et al., 1999). This would generate PEPT 2B (SEQ ID NO: 24) and PEPT 3B (SEQ ID NO: 25). Interestingly in this latter case, both cleavage products of BP-1 end with a glycine residue. This observation raises the possibility that BP-1 products are amidated by peptidylglycine alpha-amidating monooxygenase (GenBank™ accession number no. BAC22594), an enzyme whose activity has been detected in mouse calvaria, a tissue that produces BP-1 (Bimbaum et al., 1989). FIG. 6A illustrates the processing scenario for human BP-1 and depicts its putative protein products.

vi) Methods of Production of Recombinant or Synthetic BP-1 Protein Products.

The present invention provides expression vectors and host cells transformed to express the nucleic acid sequences encoding BP-1 of the invention. Expression vectors of the invention comprise a nucleic acid sequence coding for at least one BP-1, or at least one antigenic fragment thereof, or derivative or homologue thereof, or the functional equivalent of such nucleic acid sequence. Nucleic acid sequences coding for BP-1, or at least one fragment thereof may be expressed in prokaryotic or eukaryotic host cells. Suitable host cells include bacterial cells such as E. coli, insect cells, yeast, or mammalian cells such as Chinese hamster ovary cells (CHO). Suitable expression vectors, promoters, enhancers, and other expression control elements may be found in Sambrook et al. Molecular Cloning: A Laboratory Manual, second edition, Cold Spring Harbor Laboratory Press, Cold Spring Harbor, N.Y., 1989.

Whatever the producing host, the BP-1 portion of the transcription unit may be engineered to increase or control the stability or translatability of the expressed mRNA, e.g. through the insertion of exogenous cis-acting nucleic acid sequences, the replacement of poorly translated codons, the removal of untranslated sequences and/or the engineering of a proper context for the initiation of translation (Kozak, 1986). The BP-1 cDNA may also be engineered to increase the yield of secreted products, typically by replacing its signal peptide coding sequence by an exogenous nucleic acid encoding a more active signal peptide in the chosen host. Furthermore, minor modifications or variations may be introduced in the BP-1 coding sequence to enhance the stability and/or the activity of BP-1 product(s). These modifications may be made by site-directed mutagenesis or may be the result of spontaneous mutations.

Vertebrate Cell Lines

An aspect of this invention relates to modified cell lines and transgenic organisms used to produce BP-1 protein products. According to a preferred embodiment, there is provided an eukaryotic cell line having incorporated in its genome a DNA segment comprising a BP-1 coding sequence operably linked within a transcription unit. Enhancer and promoter sequences driving robust expression in a wide variety of cells are generally preferred. These include but are not limited to sequences derived from cytomegalovirus immediate-early genes (CMV; e.g. GenBank™ accession no. X03922) and Rous sarcoma virus long terminal repeat (RSV; e.g. GenBank™ accession no M83237) as well as sequences derived from widely expressed cellular genes such as chicken β-actin, human elongation factor 1α, phosphoglycerate kinase, and metallothionein. Signals for the termination and polyadenylation of transcripts are well known in the art. Examples include part of the 3' untranslated region of the bovine growth hormone gene or of the SV40 virus.

Methods to incorporate DNA segments into the genome of a cell are well known in the art. According to a preferred embodiment of the invention, the transcription unit is inserted into a plasmid containing a gene conferring resistance to a selective agent (e.g. puromycin-N-acetyltransferase conferring resistance to puromycin). The resulting construct is electroporated into cells using standard protocols. Transfection by lipofection, calcium phosphate precipitate, and microinjection are other techniques available to introduce nucleic acids into eukaryotic cells. Selection is applied on the pool of transfected cells. Surviving and growing cells are thought to have incorporated the plasmid and are cloned. Individual clones are analyzed for the production of BP-1 protein products in the culture medium. Typically, the levels of BP-1 products are determined by Western analysis or ELISA. Preferred cellular hosts include, but are not limited to, human embryonic kidney 293 cells (HEK293; American Type Culture Collection no. CRL-1573) and chinese hamster ovary cells (CHO; American Type Culture Collection no. CCL-61). It is known in the prior art how to cultivate large quantities of these cells in order to obtain large amounts of recombinant proteins. It is understood that a BP-1-producing cell line can be further engineered to express a convertase involved in BP-1 processing, thereby allowing the release of bioactive BP-1 products into the culture medium.

Transgenic Organisms

Alternatively, the transcription unit comprising the BP-1 coding sequence can be inserted into a fertilized egg (e.g. of a mouse), which is re-implanted into a pseudo-pregnant mother. DNA extracted from resulting organisms (e.g. embryos, pups or adults) is analyzed by Southern blotting to determine whether the organism is transgenic. Positive animals are bred and used to produce large quantities of BP-1 products. Ideally, the recombinant protein products should be produced in an easily collectable tissue or biological fluid (e.g. hair, milk). Furthermore, expression in tissues that are targets of BP-1 action (e.g. bone, kidney) should be limited. In order to achieve these goals, the enhancer and promoter elements of the transcription unit are chosen so that the BP-1 coding sequence is mainly expressed in the appropriate tissue (e.g. keratinocytes, mammary epithelium).

Fusion Protein in Bacteria

For some aspects of the present invention, it is desirable to produce a fusion protein comprising a BP-1 polypeptide or at least one fragment thereof or their derivatives and an amino acid sequence from another peptide or protein, examples of the latter being enzymes such as beta-galactosidase, phosphatase, urease and fusion proteins incorporating purification moieties such as His-tags, FLAG-tags, myc-epitope tags and the like. Most fusion proteins are formed by the expression of a recombinant gene in which two coding sequences have been joined together such that their reading frames are in phase.

For expression in *E. coli*, suitable expression vectors include pTRC (Amann et al. (1988) Gene 69: 301-315); pET-11d (Novagen, Madison, Wis.); pGEX (Amrad Corp., Melbourne, Australia); pMAL (N.E. Biolabs, Beverly, Mass.); pRIT5 (Pharmacia, Piscataway, N.J.); PSEM (Knapp et al. (1990) BioTechniques 8: 280-281); pQE30 (Qiagen, Germany); and pTrxFus (Invitrogen, Carlsbad, Calif.). The use of pTRC and pET-11d will lead to the expression of unfused protein. The use of pGEX, pMAL, pRIT5, pSEM, pQE30, and pTrxFus will lead to the expression of BP-1 fused to glutathione S-transferase (pGEX), maltose E binding protein (pMAL), protein A (pRIT5), truncated β-galactosidase (PSEM), hexahistidine (His6), or thioredoxin. When a BP-1, fragment, or fragments thereof is expressed as a fusion protein, it is particularly advantageous to introduce an enzymatic cleavage site at the fusion junction between the carrier protein and the BP-1 or fragment thereof. A BP-1 or fragment thereof may then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from for example Sigma Chemical Company, St. Louis, Mo. and N.E. Biolabs, Beverly, Mass.

Host cells can be transformed to express the nucleic acid sequences encoding the BP-1 of the invention using conventional techniques such as calcium phosphate or calcium chloride co-precipitation, DEAE-dextran-mediated transfection, or electroporation. Suitable methods for transforming the host cells may be found in Sambrook et al. supra, and other laboratory textbooks. The nucleic acid sequences of the invention may also be synthesized using standard techniques.

Chemical Synthesis

Homologues and derivatives of BP-1 is meant to include synthetic derivatives thereof. The nucleotide sequences encoding BP-1 can be used to chemically synthesize the entire protein or generate any number of fragments (peptides) by chemical synthesis by well known methods (e.g., solid phase synthesis). All such chemically synthesized peptides are encompassed by the present invention. Alternatively, proteins or peptides can be linked in vitro by chemical means. All such fusion protein or hybrid genetic derivatives of BP-1 or its encoding nucleotide sequences are encompassed by the present invention. Accordingly, the present invention extends to isolated BP-1, fragments thereof and their derivatives, homologues and immunological relatives made by recombinant means or by chemical synthesis.

vii) Methods of Purification of Recombinant BP-1 Protein Products.

BP-1 and fragments (peptides) thereof can be purified from cell culture medium, host cells, or both using techniques known in the art for purifying peptides and proteins, including ion-exchange chromatography, hydrophobic chromatography, gel filtration chromatography, ultrafiltration, electrophoresis and immunopurification with antibodies specific for BP-1 or fragments thereof. The terms isolated and purified are used interchangeably herein and refer to peptides, protein, protein fragments, and nucleic acid sequences substantially free of cellular material or culture medium when produced by recombinant DNA techniques, or chemical precursors or other chemicals when synthesized chemically.

Typically, recombinant proteins found in culture medium or biological fluids are purified by successive steps of chromatography according to methods known to an experimentator skilled in the art. According to a preferred embodiment of the invention, accumulation of secreted recombinant BP-1 is done by incubating engineered mammalian cells in serum-free medium, in order to limit the amount of contaminating proteins found in the medium. This medium is then diluted with column buffer (neutral HEPES-buffered saline) and passed on a cation-exchange column (e.g. Sepharose™ SP, Amersham Pharmacia Biosciences). Since the isoelectric point of human BP-1 is 9.62, it binds strongly to the negatively-charged resin in column buffer. After extensive washes with column buffer, bound proteins are eluted with a salt gradient. Fractions are collected and assayed for BP-1 immunoreactivity by ELISA. Under these conditions, the BP-1 products elute at a salt concentration of 250-300 mM. Further purification is achieved by affinity chromatography. Monoclonal or polyclonal antibodies specific to BP-1 (e.g. raised against AG2, see section v) are covalently attached to a resin, either directly (e.g. CNBR-Sepharose™) or through binding and crosslinking to immobilized protein A. In the latter case, protein A specifically binds the Fc portion of the antibodies, thereby avoiding crosslinking/inactivation of their $F(ab)_2$ portion to the resin and increasing the binding capacity of the affinity resin. BP-1-containing fractions from the ion-exchange column are pooled, diluted to a salt concentration of approximately 100 mM and passed over the affinity column at neutral pH. After washes, bound proteins are eluted under basic (pH 10) and acidic (pH 2.9) conditions. Fractions are collected, neutralized and assayed for BP-1 immunoreactivity by ELISA. BP-1-containing fractions are pooled and, if necessary, dialyzed against physiological saline and concentrated (e.g. by lyophilization).

viii) Recombinant Adenoviruses Expressing BP-1 cDNA for Gene Delivery

Since processing of BP-1 to bioactive products may occur uniquely in osteoblasts or within the bone microenvironment, it may be advantageous to express a BP-1 coding sequence in cultured osteoblasts or directly in vivo. Recombinant adenovirus particles are particularly useful to deliver a transcription unit into a whole organism or into cells that are difficult to transfect by conventional methods such as differentiated osteoblasts (Ragot et al., 1998). Standard methodology may be used to insert a transcription unit in an adenoviral genome and package the resulting recombinant adenoviral genome within an infectious viral particle. Briefly, the transcription unit comprising a BP-1 coding sequence is cloned in a plasmid between regions of the adenovirus serotype 5 genome. This plasmid is transfected, along with a replication-defective viral genome, in a cell line that can complement the replication defect, usually HEK293 cells. Homologous recombination between a plasmid and a viral genome generates a recombinant viral genome having inserted a BP-1 transcription unit. This recombinant viral genome is subsequently packaged into infectious particles. Typically, the replication-defective viral genome minimally lacks the E1 protein such that it can not replicate in infected cells unless these are HEK293 cells that endogenously synthesize the E1 protein (Louis et al., 1997). The recombinant adenovirus can be propagated in HEK293 cells to very high titers ($>10^{10}$ pfu/ml). Stocks of recombinant adenoviral particles are concentrated and purified by centrifugation on cesium chloride gradient according to standard procedures.

The resulting recombinant adenovirus can be used to infect large numbers of various cell types, including primary osteoblasts, to produce recombinant BP-1. It can also be used as a delivery system for systemic or local gene therapy or other protocols that may require overexpression of BP-1 in vivo.

ix) Therapeutic Utility of BP-1 Products

Considering the fact that BP-1 is specifically expressed in the osteoblast lineage, BP-1 products may regulate bone cell proliferation and/or bone cell differentiation and/or of osteoblast activity, via an autocrine, paracrine or endocrine pathway. BP-1 products may also control osteoclast activity via a paracrine or endocrine pathway. In either cases, pharmaceutical compositions containing a therapeutically effective amount of BP-1 products may be useful in the treatment of bone diseases, particularly in those characterized by bone loss such as osteoporosis. The BP-1 compositions may be further employed in methods for treating bone fractures or defects. Drugs that augment, mimick, antagonize or blunt the activity of BP-1 products may also be beneficial for the treatment of bone diseases. Considering the in vitro effect of our BP-1 preparations (see Example 4), drugs that antagonize or blunt the activity of BP-1 products could be particularly useful to treat osteopenic or osteoporotic conditions.

Examples of drugs that augment the activity of BP-1 products include chemicals that activate proteins involved in the transcription of the BP-1 gene, thereby upregulating its expression. Drugs that inhibit the degradation of a given BP-1 product should also lead to increased activity of this BP-1 product. Examples of drugs that mimick the activity of BP-1 products include peptidomimetics or peptides, modified or not, corresponding to fragments of BP-1 that regulate bone or kidney functions. In most cases, such drugs are agonists of the receptor that binds a given BP-1 product.

Examples of drugs that antagonize or blunt the activity of BP-1 products include a) one or a mixture of antisense oligonucleotides blocking the expression or translation of the BP-1 mRNA; b) one or a mixture of antibodies raised against a given BP-1 product quenching the activity of this product; c) an antagonist binding the cognate receptor of a given BP-1 product; d) a molecule inhibiting the enzymes responsible for the processing of the BP-1 precursor to a given product.

Phosphatonin is a putative hormone which regulates phosphate retention by kidney tubules. It has been hypothesized that phosphatonin is produced by cells of the osteoblast lineage and is a substrate for Phex, a metallopeptidase found at the cell surface of osteoblasts and osteocytes (Frota Ruchon et al., 2000; Ruchon et al., 1998; GenBank™ PID accession number g2499917). Our observations are consistent with the possibility that a given BP-1 product could have phosphatonin activity. If this is the case, then hypophosphatemia could be remedied by injection of a molecule that antagonize this activity. On the other hand, hyperphosphatemia could be remedied by injection of a molecule that stimulate or mimick phosphatonin activity. Alternatively, phosphatonin activity may be prolonged by using a drug that inhibits its degradation (e.g. inhibitors of the Phex endopeptidase activity). Such proteolysis inhibitors could be useful to treat hyperphosphatemic conditions. Thus, drugs that augment, mimick, antagonize or blunt the activity of BP-1 products may also be beneficial for the treatment of diseases characterized by abnormal serum phosphate levels.

Pharmaceutical Compositions

The present invention, therefore, provides a pharmaceutical composition comprising a therapeutically effective amount of BP-1 or derivatives, homologues or immunological relatives thereof and one or more pharmaceutically acceptable carriers and/or diluents. The active ingredients of a pharmaceutical composition comprising BP-1 is contemplated to exhibit therapeutic activity when administered in amount which depends on the particular case. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intranasal, intradermal or suppository routes or implanting (e.g., using slow release molecules). Depending on the route of administration, the active ingredients which comprise the pharmaceutical composition of the invention may be required to be coated in a material to protect the ingredients from the action of enzymes, acids and other natural conditions which may inactivate said ingredients.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders of the extemporaneous dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When at least BP-1, or at least one fragment thereof is suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be carried and may conveniently be between about 5 to 80% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (1) the unique characteristics of the active material and the particular therapeutic effect to be achieved, and (b) the limitations inherent in the art of compounding such an active material for the treatment of bone disease.

x) Screening Methods Using BP-1 Products

It is known in the prior art that proteins or peptides such as those derived from BP-1 act through binding to cognate receptors. It is possible to use labelled BP-1 products to identify such receptors. This could be done as follows. BP-1 (PROT 1, SEQ ID NO: 20) can be synthesized in the presence of labeled amino acids (e.g. tritiated L-leucine). The protein can be synthesized and labeled in vivo after transfection of a suitable host with a vector capable of expressing the BP-1 cDNA. Alternatively, transcripts can be synthesized, translated and labeled in vitro starting with a plasmid harboring the BP-1 cDNA operably linked to a DNA-dependent RNA polymerase promoter. Ideally, the in vitro translation step should be performed using rabbit reticulocyte lysates containing microsomal membranes to allow for co-translational and post-translational modifications to occur (Lingappa et al., 1979). In the case of peptides derived from BP-1 (PEPT 2A (SEQ ID NO: 22), PEPT 3A (SEQ ID NO: 23), PEPT 2B (SEQ ID NO: 24), PEPT 3B (SEQ ID NO: 25)), these can be labeled during chemical synthesis (e.g. by incorporating a biotinylated derivative of amino acids) or by adding a N-terminal tyrosine residue that can be iodinated according to standard methods (Tsomides and Eisen, 1993). The labeled BP-1 product(s) can be purified (e.g. by affinity chromatography). To screen for cognate receptors, a cDNA library is constructed according to standard protocols starting with mRNA extracted from a target organ (e.g. bone, kidney). cDNAs are cloned in an expression vector downstream of strongly active enhancer/promoter elements. The library of expression vectors is screened for BP-1 product(s) binding activity as follows. The initial step is to find a suitable host, i.e. one that does not bind the labeled BP-1 product(s) under basal conditions and in the absence of exogenous expression vectors, preferably a mammalian cell line. Examples of hosts include, but are not limited to, HEK293 cells, CHO cells, COS cells (American Type Culture Collection no. CRL-1650) and CV-1 cells (American Type Culture Collection no. CCL-70). The library is then divided into pools (e.g. 500 clones per pool), each pool is transfected into the host and incubated with the labeled BP-1 product(s). Expression vectors are extracted from cells transfected with a pool of clones that confers specific binding of the labeled BP-1 product(s). Rounds of selection are repeated until a single clone is identified. This clone encodes a putative receptor for BP-1 product(s). The receptor can be used to screen for molecules that bind to it and for molecules that modulate the binding of BP-1 product(s). Such assays can be performed on cells transfected with a vector expressing the receptor cDNA.

xi) Diagnostic Assays

Based on the features described in the invention, it can be expected that methods to assay BP-1 products or nucleic acid sequences encoding BP-1 products will be useful as diagnostic reagents i.e to diagnose or monitor diseases such as osteoporosis and disorders of phosphate metabolism. Levels of BP-1 products or expression of the BP-1 gene may correlate with the occurrence of a bone disease. For example, the amount of BP-1 products may be elevated in bones of osteoporotic patients. Various immunological methods to assay soluble extracellular proteins are well known in the prior art (e.g. radioimmunoassays, ELISA, 'sandwich' ELISA). Such methods generally uses monoclonal or polyclonal antibodies specific to the protein of interest. In the case of the present invention, these antibodies could be raised against antigenic peptides and purified as described in section v. Example 1 describes an enzyme-linked immunoadsorbent assay to quantify BP-1 products found in cell culture medium. Other immunological methods to assay BP-1 products in tissues or biological fluids may be developed by an experimentator skilled in the art. Various hybridization-based methods to assay for specific nucleic acids are well known in the prior art. In the case of BP-1 for example, RNA extracted from cells of the bone marrow can be labeled during reverse transcription (e.g. radioactively or fluorescently) and single stranded cDNA can be hybridized to an immobilized nucleic acid probe comprising part of the BP-1 sequence (e.g. oligonucleotide, cDNA).

Proteins, peptides, or antibodies of the present invention can also be used for detecting and diagnosing bone or renal conditions that involve secretion of BP-1. For example, diagnosis can be accomplished by combining blood obtained from an individual to be tested with antibodies to BP-1 and determining the extent to which antibody is bound to the sample.

Futhermore, it is expected that there are sequence polymorphisms in the nucleic acid sequence coding for BP-1, and it will be appreciated by one skilled in the art that one or more nucleotides in the nucleic acid sequence coding for BP-1 may vary due to natural allelic variation. Any and all such nucleotide variations and resulting amino acid polymorphisms are within the scope of the invention. It may also be appreciated by one skilled in the art that BP-1 maybe a member of a family of highly related genes. Nucleotide sequences and corresponding deduced amino acid sequences of any and all such related family members including BP-1 are within the scope of the invention.

EXAMPLES

As it will now be demonstrated by way of examples hereinafter, the invention provides methods to produce, partially purify and characterize the BP-1 protein products. Example 1 gives an example of a cell line secreting BP-1 protein products in the culture medium. Example 2 gives an example of a method to partially purify the BP-1 protein products from cell culture medium. Example 3 gives an example of recombinant adenovirus particles expressing a BP-1 coding sequence and uses thereof. Example 4 gives an example of treatment of primary cultures of osteoblasts with medium containing BP-1 products.

Although any methods and materials similar or equivalent to those described herein can be used in the practice or testing of the present invention, the preferred methods and materials are described.

A) Materials and Methods

The following are experimental procedures and materials that were used to describe the present invention.

Enzymes and Reagents

Restriction enzymes and DNA-modifying enzymes were purchased from New England Biolabs (Cambridge, Ma.) unless otherwise stated. Synthetic oligonucleotides were obtained either from Hukabel Ltd. (Montreal, Quebec, Canada) or MWG Biotech Inc. (High Point, N.C.). Cell culture reagents were from Life Technologies (subsidiary of Invitrogen, Carlsbad, Calif.) unless otherwise stated. Chemicals were obtained either from Roche Molecular Biochemicals (Laval, Canada), Calbiochem (San Diego, Calif.) or Sigma (St. Louis, Mo.). Radiochemicals were purchased from Amersham Pharmacia Biotech (Baie d'Urfé, Canada). Sequencing of DNA was done using the Dye terminator cycle sequencing DTCS™ sequencing kit (Beckman Coulter, Fullerton, Calif.) and a Beckman CEQ 2000 automated sequencer.

RNA Extraction and Analysis

Total RNA was purified either by the guanidium isothiocyanate/acid phenol method (Chomczynski and Sacchi, 1987) or using the RNEASY™ kit according to the manufacturer's instructions (Qiagen, Mississauga, Canada). PolyA+ RNA was purified using the Oligotex™ kit according to the manufacturer's instructions (Qiagen). Northern analysis were performed as follows. RNA was electrophoresed on 1.2% agarose/1.2% formaldehyde gels in 1×MOPS buffer (10 mM 3-(N-morpholino)propanesulfonic acid, 4 mM sodium acetate, 0.5 mM EDTA, pH 7) and transferred onto a nylon membrane (Osmonics, Westborough, Ma.) by capillarity in 20×SSC. After UV crosslinking, the blot was incubated in Church buffer (Church and Gilbert, 1984) for 4-8 hours at 63° C. and hybridized overnight in Church buffer containing approximately 1 ng/ml of ca155-cap1-c2-neg306 fragment that had been labelled with [$\alpha^{32}$P]dCTP by random priming.

Cloning of Full Length Mouse cDNA Corresponding to ca155-cap1-c2-neg306

First, an expression vector was generated as follows. A 5498 bp SacII-ApaI fragment of pQBI25fc3 (qBiogene, Montreal, Canada) was blunted and ligated unto itself to generate pCMVneo. Complementary oligonucleotides 30-11

(SEQ ID NO. 35) and 30-12 (SEQ ID NO. 36) were annealed and cloned in pCMVneo previously digested with BamHI and EcoRI and blunted using the Klenow fragment of DNA polymerase 1. The resulting plasmid is pCMVneoXN. The first strand of cDNAs was reverse transcribed at 42° C. from 5 µg of e15.5 mouse calvaria total RNA using a $dT_{15}$ primer-linker (33-1V, SEQ ID NO: 37) and Superscript II™ (Invitrogen, Carlsbad, Calif.). After RNAse H treatment (Roche Molecular Biochemicals, Laval, Canada), 3/10 of the first strand cDNA preparation was subjected to 25 cycles of PCR using DNA polymerases from the Titan™ RT-PCR kit, forward primer 25-10G (25-10G, 5'-aaacgctctgacftctcacaagatg-3', SEQ ID NO. 38) and reverse primer 18-30V (18-30V, 5'-gagatgaattcctcgagc-3', SEQ ID NO. 39). Cycling conditions were as follows: 94° C. for 45 seconds, 54° C. for 30 seconds, 68° C. for 3 minutes. PCR products were cloned in pCMVneoXN to generate GD25. Bacterial colonies were hybridized with a ca155-cap1-c2-neg306 radioactive probe. Inserts from positive colonies were sequenced.

Cloning of Vertebrate Homologs of BP-1

PolyA+ RNA from human bone marrow was purchased from Clontech Inc. (Palo Alto, Calif.). RT-PCR was performed on 50 ng of polyA+ RNA using forward primer 18-131G (SEQ ID NO. 40) and reverse primer 19-9G (SEQ ID NO. 41) and Titan™ one tube RT-PCR system according to the manufacturer's instructions (Roche Molecular Biochemicals). Cycling conditions (40 cycles) were as follows: 94° C. for 1 minute, 54° C. for 1 minute, 68° C. for 1 minute. PCR products (predominant band at approximately 400 bp) were cloned in pBluescript 11 KS (Stratagene, La Jolla, Calif.) and inserts from randomly chosen colonies were sequenced.

Total RNA was extracted from UMR-106 cells (CRL-1661, American Type Culture Collection, Manassas, Va.). This cell line is derived from a rat osteosarcoma and possesses characteristics of the osteoblast lineage (Partridge et al., 1983). The first strand of cDNAs was reverse transcribed at 42° C. from 5 µg of total RNA using 33-1V and Superscript II™ (Invitrogen). After RNAse H treatment (Roche Molecular Biochemicals) and purification using the minElute kit (Qiagen), ¼ of the first strand cDNA preparation was subjected to 35 cycles of PCR using the DNA polymerases from the Titan™ RT-PCR kit, forward primer 18-131G and reverse primer 18-30V. Cycling conditions were as follows: 94° C. for 1 minute, 48° C. for 1 minute, 68° C. for 1.5 minute. RT-PCR products were purified using the minElute kit. 1/6 of the initial PCR reaction was subjected to 35 cycles of semi-nested PCR using the DNA polymerases from the Titan™ RT-PCR kit, forward primer 18-131G and reverse primer 21-9G (SEQ ID NO. 42). PCR products (predominant band at approximately 500 bp) were cloned in pBluescript II KS (Stratagene, La Jolla, Calif.) and inserts from randomly chosen colonies were sequenced.

Total RNA was extracted from the vertebrae and surrounding muscles of a 2-month old birman python (~130 g) using the TriZol™ reagent (Invitrogen). The first strand of cDNAs was synthesized at 42° C. for 1 hour from 4 µg of total RNA using 0.5 µg of oligo-$dT_{18}$ and 200U Superscript II™ (Invitrogen) in a total volume of 20 µl. After RNAse H treatment (2U added, Roche Molecular Biochemicals) and purification using the QIAQuick kit (Qiagen) with 30 µl of elution buffer, the first strand cDNA preparation (2 µl) was subjected to 33 cycles of PCR using Taq DNA polymerase, forward primer 23-4V (SEQ ID NO. 44) and reverse primer 23-6V (SEQ ID NO. 45). Cycling conditions were as follows: 94° C. for 30 seconds, 56° C. for 30 seconds, 72° C. for 40 seconds. RT-PCR products were purified using the minElute kit. PCR products (predominant band at approximately 130 bp) were cloned in pBluescript II KS (Stratagene, La Jolla, Calif.) and inserts from randomly chosen colonies were sequenced.

In Situ Hybridization

In situ hybridization on paraformaldehyde-fixed paraffin-embedded tissue sections was performed according to standard procedures (for example, see Wilkinson and Nieto, 1993). Briefly, [$\alpha^{35}S$]UTP-labeled cRNA probe were synthesized in vitro from 0.5 µg of purified linearized template DNA using DNA-dependent RNA polymerase (SP6, T7 or T3 RNA polymerase). After phenol/chloroform extraction and ethanol precipitation, quality of the probe was assessed by denaturing 4% polyacrylamide gel electrophoresis. Tissue sections were deparaffinized, rehydrated, treated with 5 µg/ml of proteinase K (Roche Molecular Biochemicals) for 15 minutes in 50 mM Tris-HCl pH 8/5 mM EDTA, refixed in 4% paraformaldehyde, acetylated with 0.25% (v/v) acetic anhydride in 0.1 M triethanolamine pH 8, dehydrated and air-dried. Prehybridization was carried out for 2-4 hours at room temperature in 4×SET, 1× Denhardt's solution, 0.5 mg/ml ssDNA, 0.6 mg/ml yeast RNA, and 50% deionized formamide. 1×SET is 0.15M NaCl, 0.03M Tris-HCl pH 8 and 2 mM EDTA. 1× Denhardt's solution is 0.02% (w/v) Ficoll, 0.02% (w/v) polyvinylpyrrolidone, 0.1% (w/v) BSA fraction V. ssDNA is salmon sperm DNA that has been sonicated to obtain fragments averaging 2 kb, purified by phenol/chloroform extraction/ethanol precipitation/dialysis and denatured by boiling. Hybridization was carried out for 12-16 hours at 54° C. with 40,000 cpm/µl of CRNA probe in 4×SET, 1× Denhardt's solution, 0.1 mg/ml ssDNA, 0.1 mg/ml yeast RNA, 10% dextran sulfate, 10 mM DTT, 0.1% SDS, and 50% deionized formamide. High stringency washes were performed as follows: formamide wash for 30 minutes at 55° C. and 30 minutes at 62° C.; 20 µg/ml RNAse A treatment in 3.5×SSC, 30 minutes, 37° C.; formamide wash for 30 minutes at 62° C. Formamide wash is 50% deionized formamide/0.15M NaCl/0.15M sodium citrate/10 mM DTT. After rinses, slides were dehydrated, dipped in Kodak NTB-2 liquid emulsion (Intersciences, Markham, Canada), developed after 3-4 weeks of exposition and counterstained by hematoxylin-eosin.

Cloning of Mouse BP-1 into a Mammalian Expression Vector

To optimize expression of BP-1 in heterologous systems, a vector expressing the coding sequence of mouse BP-1 was obtained as follows. A 411 bp fragment was amplified from 10 ng of plasmid GD25 using forward primer 25-10G (SEQ ID NO: 38) and reverse primer 24-10G (SEQ ID NO: 43). The PCR reaction contained 25 pmoles/µl of each primer, deoxynucleotides at 200 µM, dithiothreitol at 5 mM, the buffer and the enzyme mix from the Titan™ one-step RT-PCR kit (Roche Molecular Biochemicals). Cycling conditions were as follows: 94° C. for 30 seconds, 56° C. for 30 seconds, 68° C. for 30 seconds. The PCR product was cloned in the unique Pmel site of pCMVneoXN to generate GD23. The identity of the insert was verified by DNA sequencing.

Production and Purifcation of Antisera

Peptides were synthesized, purified and coupled to activated keyhole lympet hemocyanin via sulfhydryl groups. The peptide/carrier complex was mixed with complete Freund's adjuvant and injected subcutaneously to rabbits on day 1. On days 21, 35 and 49, the peptide/carrier complex mixed with incomplete Freund's adjuvant was again injected. Blood samples were collected on days 44 and 59 to determine the antiserum titer by ELISA. Animals were exsanguinated on day 63. Immunoglobulins were precipitated from pooled antisera and purified by peptide affinity chromatography according to standard protocols (Affinity Bioreagents, Golden, Co.).

Cell Culture and Transfection

HEK293A cells (purchased from Quantum Biotechnologies, Montreal, Canada) are grown in Dulbecco modified essential medium supplemented with 10% (v/v) fetal bovine serum, 100 U/ml penicillin, 100 mg/ml streptomycin (referred hereafter as complete medium). Cells are passaged when reaching 80-95% confluence by incubating with 0.05% (v/v) trypsin/0.5 mM EDTA (Wisent Inc., St-Bruno, Canada). Lipofection is performed as follows. Lipid-DNA complexes (containing typically 1 μg of DNA) are formed using the Effectene™ reagent (Qiagen) according to the manufacturer's instructions. Cells are transfected the day after plating (typically 18,700 cells/cm$^2$) by adding the lipid-DNA complex to the culture medium. After a 6 hour incubation, the medium is changed and cells are usually processed after 48 hours.

Immunofluorescence

All incubations and washes are done at room temperature. Cells are rinsed with PBS and fixed with 2% (w/v) paraformaldehyde in PBS. Cells are washed with PBS. For detection of intracellular protein, cells are permeabilized by incubation in 0.1% TRITON X-100™ in PBS for 4 minutes and washed twice with PBS. Cells are then incubated in 50 mM NH$_4$Cl in PBS for 10 minutes at room temperature and washed with PBS. Cells are incubated in PBS supplemented with 0.1% (w/v) bovine serum albumin fraction V and 2% (w/v) dried milk for 1 hour. Cells are then incubated for 1 hour with a 1/100 dilution (v/v) of antiserum raised against BP-1 in PBS supplemented with 0.1% (w/v) bovine serum albumin and 0.5% (w/v) dried milk. Cells are washed twice with PBS and incubated for 1 hour in 1/200 dilution of goat anti-mouse coupled to fluorescein isothiocyanate (Sigma) in PBS supplemented with 0.1% (w/v) bovine serum albumin. Cells are washed twice and observed by fluorescence microscopy.

Western Analysis

Cell extracts. Cells are rinsed with PBS. Membrane proteins are solubilized in 0.1 ml of Lysis buffer (50 mM Tris-Cl pH 8.0, 150 mM NaCl, 2 mM EDTA, 1% IGEPAL-630™ and 1% (v/v) protease inhibitor cocktail (Sigma)). Cell debris and insoluble material are pelleted by centrifugation at 12,000 g for 5 minutes at 4° C. Protein concentration in the supernatant is determined using the Bradford assay according to the manufacturer's instructions (Bio-Rad, Hercules, Calif.).

Medium. 24 hours post-transfection, medium is replaced by medium containing 0.5% (v/v) fetal bovine serum. The following day, this medium is collected and centrifuged at 12,000 g for 5 minutes at 4° C. to remove cell debris. Proteins in the supernatant are precipitated by adding trichloroacetic acid at a final concentration of 10% (v/v) and incubating on ice for 1 hour. After centrifugation at 12,000 g for 15 minutes at 4° C., the pellet is washed once with cold acetone, dried briefly and resuspended in 24 μl of Lysis buffer.

Proteins are boiled for 5 minutes in the following Laemmli 1× solution: 50 mM Tris-HCl, pH 6.8, 100 mM dithiothreitol, 2% sodium dodecyl sulfate, 0.1% bromophenol blue, 10% glycerol. Proteins are electrophoresed on denaturing polyacrylamide gel and transferred to 0.2 μm nitrocellulose (Protran®, Schleicher&Schnell, Keene, N.H.) according to standard Western protocols. The nitrocellulose membrane is incubated overnight in Tris-buffered saline (TBS; 25 mM Tris-HCl, pH 7.4, 137 mM NaCl, 2.7 mM KCl) supplemented with 5% (w/v) dried milk and 0.1% (v/v) TWEEN-20™. It is then incubated for 1 hour at room temperature with a 1/800 dilution (v/v) of antiserum raised against BP-1 in TBS supplemented with 2.5% (w/v) dried milk and 0.1% (v/v) TWEEN-20™. The membrane is washed twice with TBS supplemented with 0.1% (v/v) TWEEN-20™. It is then incubated for 1 hour at room temperature with goat anti-mouse coupled to horseradish peroxidase (Sigma) diluted 1/30,000 in TBS supplemented with 2.5% (w/v) dried milk and 0.1% (v/v) TWEEN-20™. The membrane is washed twice with TBS supplemented with 0.1% (v/v) TWEEN-20™. Detection of the protein bound to the antibody complex is performed with the ECL™ reagent according to the manufacturer's instructions (Amersham Pharmacia Biotech, Baie d'Urfé, Canada).

Primary Culture of Rat Calvarial Osteoblasts

Calvariae were dissected from embryonic rats from days 19-21 of gestation. Osteoblasts were isolated by 5 successive digestions of the tissues with a mix of collagenase (2 mg/ml, Worthington, N.J.), trypsin (0.05% w/v, Roche Molecular Biochemicals, Ind.) and EDTA (0.02% w/v) for 20 minutes with agitation at 37° C. Cells from digests 2 to 5 were seeded at 10,000 cells/cm$^2$ and cultured in AMEM (Invitrogen, Carlsbad, Calif.) supplemented with 10% (v/v) FBS, 20 mM HEPES pH 7.4, 2 mM L-glutamine, 5 mM β-glycerophosphate, 50 μg/ml ascorbic acid, 100U/ml penicillin, 100 μg/ml streptomycin. Medium was changed every 2-3 days.

Incorporation of $^{45}$Ca into Primary Cultures of Rat Calvarial Osteoblasts

Cells were incubated in medium containing 1 μCi/ml $^{45}$CaCl$_2$ to assay calcium uptake into mineralized matrix. Medium was collected 48 hours later from each well and added to 4 ml of scintillation cocktail, and counted on a scintillation counter. The cells were washed twice in PBS then scraped into 5001 μl of lysis buffer (20 mM Tris, 0.5 mM MgCl$_2$, 0.1% (v/v) Triton X-100™). Cellular debris was spun out, the lysis buffer removed and stored and the pellet resuspended in 1 ml 0.5M EDTA. The pellet in EDTA was placed overnight on a rocking platform then the debris spun out and the EDTA solution removed and stored. The pellet was then resuspended in 1 ml 0.5M NaOH and placed overnight on a rocking platform. The remaining cell debris was spun out and the NaOH removed and stored. To ascertain $^{45}$Ca incorporation, 100 μl of the lysis buffer and 500 μl of the EDTA and NaOH fractions were counted in 4 ml of scintillation fluid. The proportion of $^{45}$Ca taken up into the cells in each well was then calculated as a percentage of the total counts in each well.

B) Example 1

Cell Lines Secreting BP-1 Protein Products in the Culture Medium

The expression vector used to obtain stable cell lines producing BP-1 is schematized on FIG. 7A. Plasmid RC33 (see provisional patent application and international patent application PCT/CA02/00997) was digested with KpnI and EcoRI and plasmid GD23 (see Materials and Methods) was digested with KpnI and MluI. Both digests were treated using the Klenow fragment of DNA polymerase I to blunt the 5' protruding extremities generated by EcoRI and MluI. The 5194 bp fragment of the RC33 digest and the 473 bp fragment of the GD23 digest were purified and ligated. The resulting vector is designated GD46. A similar vector comprising the coding sequence for human BP-1 was obtained and is designated GD45. One of the transcription unit of GD46 comprises the cytomegalovirus immediate early gene enhancer/promoter regions (700) followed by the coding sequence for mouse BP-1 (701) and a bovine growth hormone polyadenylation signal (702). GD46 also comprises a transcription unit to confer resistance to puromycin (703).

To obtain cell lines having integrated one or more copies of GD46 in its genome, 3.5 million of HEK293 cells were electroporated at 600V/cm with a mixture of 3.5 µg of ScaI-linearized expression vector and 15 µg of denatured salmon sperm DNA. Cells were plated and selection (2.5 µg/ml puromycin) was applied 24 hours later. The concentration of puromycin was reduced to 0.2 µg/ml on day 4 and colonies were picked on day 11. Clones were grown until confluence in 24-well plates. At this time, cells were incubated in 0.5 ml of medium without serum for 48 hours. One-fifth (100 µl) was analyzed by ELISA as follows. One volume (100 µl) of 2× carbonate buffer (13 mM $Na_2CO_3$/35 mM $NaHCO_3$) was added to the sample. Samples were transferred in wells of a high-binding capacity polystyrene plate (Corning, USA) and incubated 1 hour at 37° C. The medium was then aspirated and the well was washed once with TBST (Tris-buffered saline pH 7.4 [TBS; 100 mM Tris], 0.1% (v/v) Tween-20™). Non-specific binding sites were blocked for 1 hour at 37° C. with 300 µl of TBS supplemented with 5% (w/v) of non fat milk. After 5 washes with TBST, incubation proceeded for 1 hour at 37° C. with 200 µl of a 1/2500 dilution of the affinity-purified antibody against the C-terminal portion of BP-1 in TBST supplemented with 2.5% (w/v) of non fat milk. The plate was then washed 5 times with TBST. Samples were incubated for 1 hour at 37° C. with 200 µl of a 1/30,000 dilution of anti-rabbit IgG coupled to horseradish peroxydase (Sigma, St. Louis, Mo.). After 5 washes with TBST, the antibody complex was revealed with Sigma Fast™ o-phenylenediamine dihydrochloride according to the manufacturer's recommendations. Reactions were stopped by adding 25 µl of 5N sulfuric acid per well. Absorbance at 490 nm was determined using a plate reader. Known quantities of antigenic peptide are also assayed to determine a standard curve (FIG. 7B). The clones of GD46 transfectants secreting immunoreactive BP-1 products in the culture medium were expanded. The amount of BP-1 products released by each clone was calculated by regression analysis after assaying varing volumes of culture medium. The highest expressor (clone 293-GD46-7) was found to secrete 8 pg of BP-1 products per cell in the culture medium in 48 hours. This corresponds to a production of approximately 10 mg/l for a confluent monolayer in a 175 $cm^2$ flask. We also obtained a cell line overexpressing the human BP-1 coding sequence (293-GD45-58B). Confluent 175 $cm^2$ monolayers of these cells secrete approximately 0.6 mg of BP-1 products per liter of culture medium in 48 hours.

To ascertain that the cell lines we derived were of monoclonal origin and would not be diluted by non BP-1-expressing cells upon passaging, immunofluorescence analysis was performed on confluent monolayers of 293A-GD46-7 using an antibody directed against the C terminal portion of BP-1. BP-1 immunoreactivity was seen in the secretory apparatus in over 98% of the cells.

C) Example 2

Method to Partially Purifly the BP-1 Protein Products from Cell Culture Medium

Six million cells stably overexpressing mouse BP-1 (clone 293-GD46-7) were seeded in a 175 $cm^2$ flask and grown for 48 hours in DMEM supplemented with 10% FBS, at which stage the monolayer was approximately 90% confluent. The cells were then washed 2 times with pre-warmed phosphate buffered saline and once with serum-free DMEM. The cells were incubated for 48 hours in 20 ml of serum-free DMEM. The medium was then collected and spun down at 800 g for 2 minutes to remove floating cells and debris. All subsequent procedures were performed at 4° C. using a BioRad Bio-Logic™ LP Chromatography system. The conditioned medium containing BP-1 products was first diluted 2-fold with equilibration buffer (Buffer A: 25 mM HEPES pH 7.8 and 100 mM NaCl) and filtered through a 0.45 µm Filtropur™ S membrane. The diluted medium was then loaded at a flow rate of 2 ml/min on a column (1.5 cm×20 cm) packed with 3.5 ml gel bed of a Sepharose™ SP cation exchange resin (Amersham-Pharmacia Biosciences). The flow-through was collected until the absorbance at 280 nm returned to baseline. The resin was washed with 5 bed volume of Buffer A at 2 ml/min. The bound-proteins were eluted at 1 ml/min with 50 ml of a linear gradient from 0-100% of Buffer B (25 mM HEPES pH 7.8 and 1 M NaCl). Fractions of 1 ml were collected and monitored for the presence of BP-1 by ELISA (see Example 1). The fractions containing BP-1 were pooled and concentrated 10-fold on an Amicon Centriplus™ YM-3 (3 kDa cut-off membrane) by centrifugation at 3400 g at 4° C. No significant loss of BP-1 immunoreactivity occurred during this concentration procedure.

Figure 8:
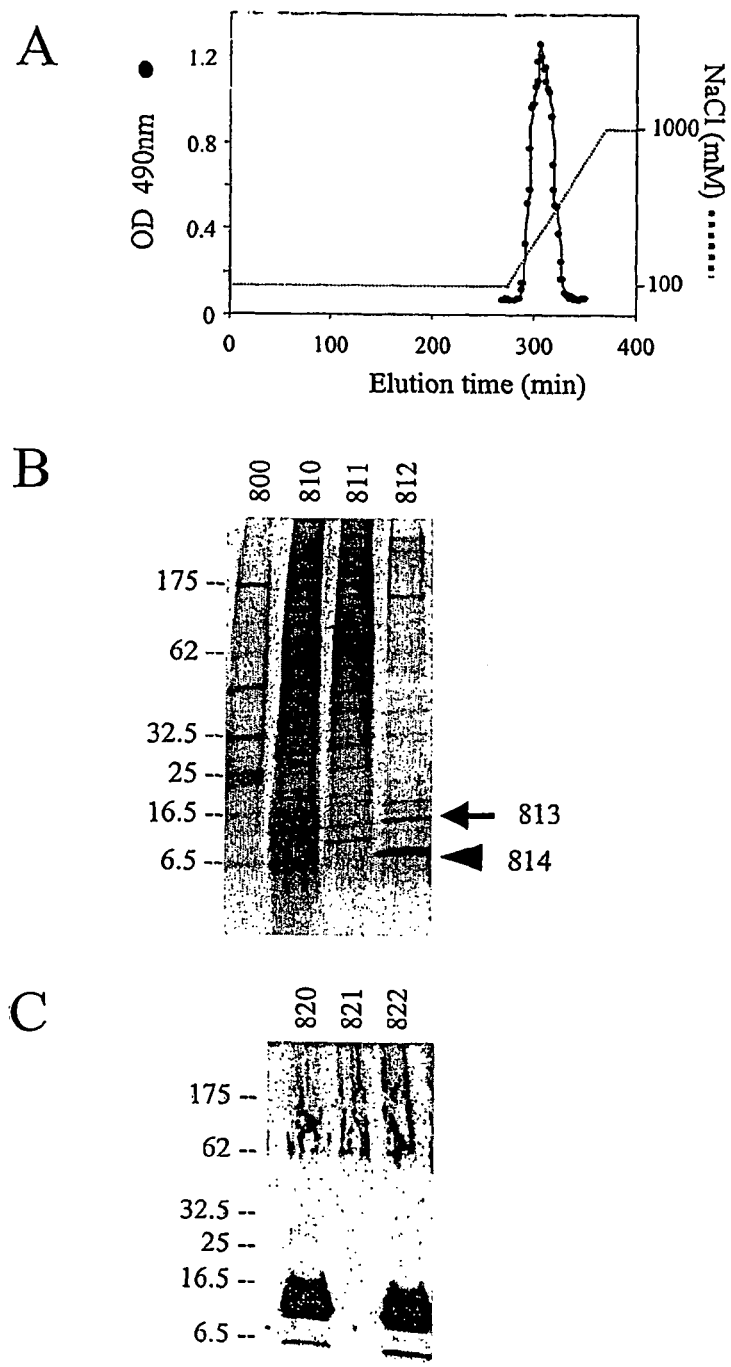
FIG. 8A shows the levels of BP-1 immunoreactivity in fractions collected from a cation-exchange chromatography column after passage of conditioned medium from 293-GD46-7 cells overexpressing the mouse BP-1 coding sequence.
FIG. 8B is a picture of a silver-stained polyacrylamide gel showing the proteins found in the conditioned medium from 293-GD46-7 cells (lane 810), in the flow through from a cation-exchange chromatography column (lane 811) and in BP-1-immunoreactive fractions from the same column (lane 812). Arrow 813 points to a BP-1 product. Arrowhead 814 points to aprotinin, a contaminating protease inhibitor included in the conditioned medium before the chromatographic step.
FIG. 8C shows the result of a Western analysis performed on conditioned medium from 293-GD46-7 cells (lane 820), on the flow through from a cation-exchange chromatography column (lane 821) and on BP-1-immunoreactive fractions from the same column (lane 822).

FIG. 8 shows the results of the initial steps of the purification scheme described above. The fractions collected from the cation-exchange column were individually assayed for BP-1 immunoreactivity by ELISA (FIG. 8A). The input (conditioned medium 0.9% of total), the flow through (0.9% of total) and BP-1-containing fractions (0.8% of total) were analyzed by SDS-PAGE 10-20% (FIG. 8B, lanes 810, 811, 812, respectively). After electrophoresis, the gel was stained by Plus One™ silver staining kit (Amersham Pharmacia Biosciences). Lane 800 shows the migration of molecular weight markers. Arrow 813 points to a BP-1 product. Arrowhead 814 points to aprotinin, a contaminating protease inhibitor included in the conditioned medium before the chromatographic step. A duplicate gel was transferred onto nitrocellulose membrane and BP-1 products were revealed by immunostaining (FIG. 8C, lane 820:input, lane 821:flow through, lane 822: BP-1-containing fractions). Results indicate that the bulk of the proteins in the culture medium do not bind the cation exchange column (compare lanes 810 and 811). By Coomassie and silver staining, we estimate that these initial steps of purification allowed a 25-fold enrichment in BP-1 products. As can be seen on the Sepharose™ SP elution profile (FIG. 8A), BP-1 products eluted at a salt concentration of approximately 300 mM NaCl. Importantly, the immunoreactive fractions contain products of lower apparent molecular weight (lane 822, band at ~6 kD) in addition to the ~13 kD form of BP-1. This indicates that the partial purification scheme described above can enrich for all BP-1 products secreted by an overexpressing cell line.

D) Example 3

Recombinant Adenovirus Particles Expressing the BP-1 Coding Sequence and Uses Thereof This example illustrates the various functionalities of an adenovirus-based expression vector designed according to the present invention. To obtain a 'shuttle' vector for inserting a transcription unit into an adenoviral genome, a 1689 bp StuI-NaeI fragment from GD23 (see Materials and Methods) was blunted and cloned in the EcoRV site of pQBI-AdBN (qBiogene, Montreal, Canada) which had been previously engineered to replace the unique ClaI site with a unique PmeI site. The resulting vector is designated GD28b and comprises a transcription unit for mouse BP-1 coding sequence (901) flanked by nucleotides 1-102 (902) and nucleotides 3334-5779 (903) of the Adenovirus serotype 5 genome (GenBank™ accession number 9626187). A map of GD28b is given in FIG. 9A.

The transcription unit for BP-1 comprised in GD28b was incorporated in an adenoviral genome by in vivo homologous recombination. This was done by co-transfecting 5 µg of Pmel-linearized GD28b with 5 µg of AdCMVIacZΔE1/ΔE3, a replication-defective genome obtained commercially (qBiogene, Montreal, Canada). Co-transfection of DNA molecules in HEK293 cells was carried out by means of a calcium phosphate precipitate using standard protocols. Two days post-transfection, cells were overlaid with medium containing 1.25% (w/v) low melting agarose. Recombinant viral genome resulting from homologous recombination between GD28b and the replication-defective adenoviral genome can be propagated in HEK293 cells, as indicated by the appearance of viral plaques starting at day 8 post-infection. Plaques were picked at day 14 post-transfection. After elution, viral particles (1/10 of the elutate) were used to infect 3×10$^5$ HEK293 cells to assay for BP-1 expression. This was done by measuring BP-1 immunoreactivity by ELISA in 1/10 of the culture medium 2 days post-infection. Expression of BP-1 was also confirmed by Northern and Western analysis. A stock of recombinant adenoviral particles (Ad5GD28b) was obtained after 2 successive rounds of plaque-purification according to standard protocols. This stock was amplified on HEK293 cells. At the time of full cytophathic effect, the infected cells were harvested and the viral particles were purified on a discontinuous cesium chloride gradient and on a continuous cesium chloride gradient according to standard protocols (O.D.260 Inc., Boise, Id., USA).

The following experiment was performed to assess the efficiency of BP-1 gene transfer in osteoblasts by recombinant adenoviruses. Primary cultures of osteoblasts were grown in vitro (see Materials and Methods). Cells reached confluence 5 days after seeding, at which time they started depositing an extracellular collagen matrix. Mineralization of this matrix was routinely visible around days 13-15. At day 11, cells were infected with CsCl-purified Ad5GD28b at a multiplicity of infection of 100 pfu/cell for 3 hours. Relative levels of BP-1 products were determined by ELISA on aliquots (1/40) of culture medium taken 2, 4, 7 and 10 days post-infection (FIG. 9B). Results show that BP-1 immunoreactivity is detected as early as 2 days post-infection, peaks at day 4 and is still detectable 10 days post-infection. These results indicate that a preparation of Ad5GD28b can be used to express high levels of BP-1 in osteoblasts.

E) Example 4

Treatment of Osteoblasts with Medium Containing BP-1 Products

This example demonstrates the effects of treating primary cultures of osteoblasts with medium containing BP-1 products. The BP-1-containing medium was obtained by transient transfection of 1.5 million HEK293A cells with 2 µg of GD23, an expression vector for mouse BP-1 cDNA. Control medium was obtained by similarly transfecting pCMVneo, a control expression vector. At 24 hours post-transfection, cells were washed twice with serum-free αMEM. The transfected cells were then incubated for 48 hours in primary culture medium. BP-1 products were characterized by Western analysis using an antiserum raised against a C-terminal portion of BP-1 (SEQ AG3). The concentration of BP-1 products was estimated at 5-10 µg/ml with the bulk of immunoreactive protein having an apparent molecular weight of ~13 kD and a minor fraction having an apparent molecular weight of ~6 kD after SDS-PAGE (e.g. FIG. 6B).

Figure 10:
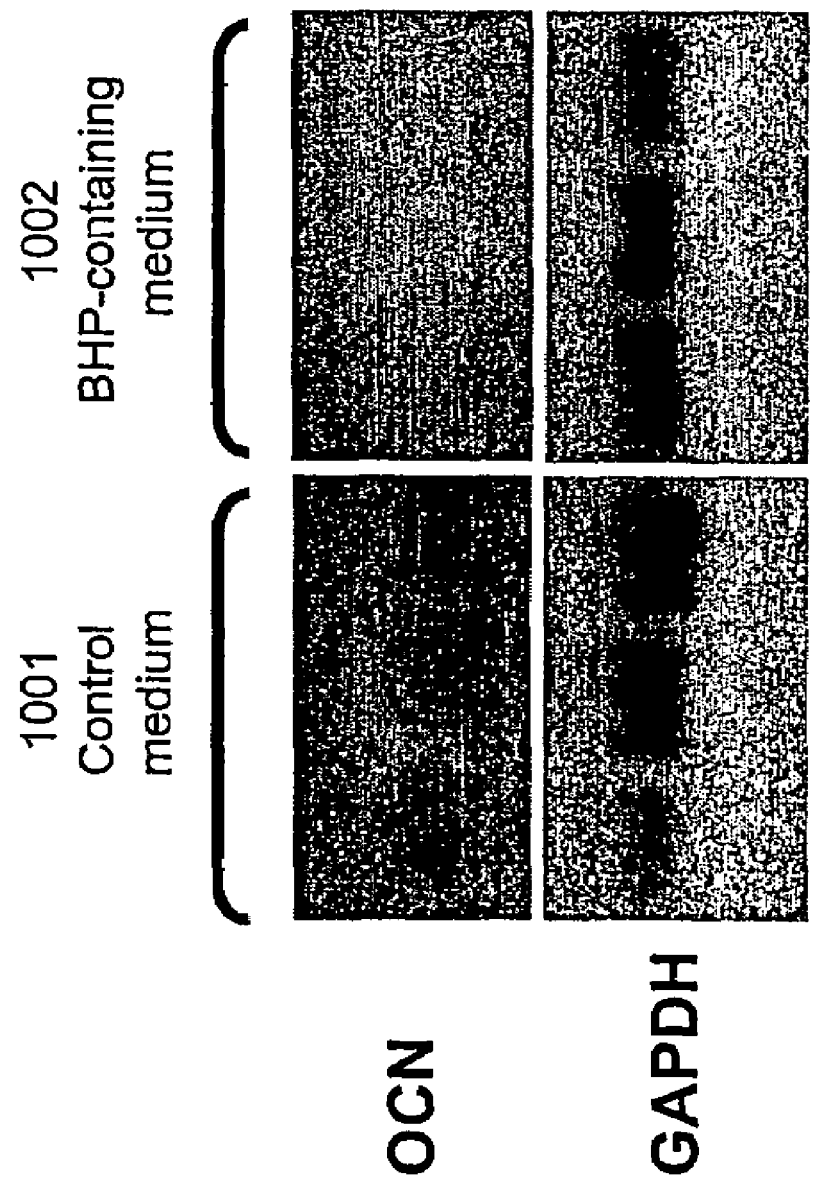
FIG. 10 shows the result of a Northern analysis to detect osteocalcin (OCN) in total RNA extracted from primary cultures of osteoblasts treated chronically with control medium (1001) or medium containing BP-1 products (1002). The levels of a control messenger (GAPDH) are also shown.

Primary cultures of osteoblasts prepared as described in Materials and Methods were cultivated in a 1/6 (v/v) dilution of either BP-1-containing or control medium. β-glycerophosphate (10 mM) was added to the culture medium from day 12. The effect of the treatment was determined by measuring osteocalcin expression and matrix mineralization, both markers of the mature osteoblastic phenotype. As shown in FIG. 10, treatment with BP-1-containing medium (1002) for 18 days completely suppressed osteocalcin (OCN) expression compared to treatment of cells with control medium (1001). Glyceraldehyde 3-phosphate dehydrogenase (GAPDH) expression in the two cell populations was similar, demonstrating no general effects on the cell populations. Incorporation of $^{45}$Ca was also markedly reduced in the cells treated with BP-1-containing medium compared to cells treated with control medium (~60%, p<0.01). These results suggest that BP-1 products restrict the progression from early to late stage osteoblasts.

REFERENCES

Throughout this paper, reference is made to a number of articles of scientific literature which are listed below.

Aarder, E. M., Burger, E. H., Nijweide, P. J. (1994) Function of osteocytes in bone, J. Cell Biochem., 55, 287-299

Bagi, C. M., DeLeon, E., Brommage, R., Adams, S., Rosen, D., Sommer, A. (1995) Systemic administration of rhIGF-I or rhIGF-I/IGFBP-3 increases cortical bone and lean body mass in ovariectomized rats, Bone, 16(Suppl.), 263S-269S Baron, R. (1999) Anatomy and ultrastructure of bone, in Primer on the Metabolic Bone Diseases and Disorders of Mineral Metabolism, ed. Lippincott Williams &Wilkins, Philadelphia, pp. 3-10

Birnbaum, R. S., Howard, G. A., Roos, B. A. (1989) Ontogeny of peptidylglycine alpha-amidating monooxygenase activity in rapidly mineralizing bone from neonatal mouse, Endocrinology, 124, 3134-3136

Chomczynski P, Sacchi N. (1987) Single-step method of RNA isolation by acid guanidinium thiocyanate-phenol-chloroform extraction, Anal Biochem., 162, 156-9.

Church GM, Gilbert W. (1984) Genomic Sequencing, Proc Natl Acad Sci U S A, 81, 1991-5

Denault, J.-B., Leduc, R. (1996) Furin/PACE/SPC1: a convertase involved in exocytic and encodytic processing of precursor proteins, FEBS Lett., 379, 113-116

Ducy, P. (2000) Cbfa1: a molecular switch in osteoblast biology, Dev. Dyn. 219, 461-471

Ducy, P., Amling, M., Takeda, S., Priemel, M., Schilling, A. F., Biel, F. T., Shen, J., Vinson, C., Rueger, J. M., Karsenty, G. (2000) Leptin inhibits bone formation through a hypothalamic relay: a central control bone mass, Cell, 100, 197-207

Frota Ruchon, A., Tenenhouse, T. S., Marcinkiewicz, M., Siegfried, G., Aubin, J. E., Desgroseillers, L., Crine, P., Boileau, G. (2000) Developmental expression and tissue distribution of phex protein: effect of the hyp mutation and relationship to bone markers, J. Bone Miner. Res., 15, 1440-1450.

Henikoff S., Henikoff J. G.; RT "Automated assembly of protein blocks for database searching."; RL Nucleic Acids Res. 19:6565-6572(1991).

Hopp, T. P., Woods, K. R. (1981) Prediction of protein antigenic determinants' from amino acid sequences, Proc Natl Acad Sci USA, 86, 152-156

The Hyp consortium (1995) A gene (PEX) with homologies to endopeptidases is mutated in patients with X-linked hypophosphatemic rickets, Nat. Genet. 11, 130-6

Inagami T, Misono K S, Grammer R T, Fukumi H, Maki M, Tanaka I, McKenzie J C, Takayanagi R, Pandey K N, Parmentier M. (1985) Biochemical studies of rat atrial natriuretic factor, Clin Exp Hypertens A, 7, 851-867

Karlin S, Altschul S F, Proc Natl Acad Sci USA 1990 March, 87:2264-8;

Karlin S, Altschul S F, Proc Natl Acad Sci USA 1993 Jun. 15;90(12):5873-7; Altschul, SF (1993), J. Mol. Evol. 36:290-300

Kozak M (1986) Point mutations define a sequence flanking the AUG initiator codon that modulates translation by eukaryotic ribosomes, Cell, 44, 283-292

Kumar, R. (2000) Tumor-induced osteomalacia and the regulation of phosphate homeostasis, Bone, 27,:333-8

Lingappa V. R., Cunningham B. A., Jazwinski S. M., Hopp T. P., Blobel G., Edelman G. M. (1979) Cell-free synthesis and segregation of beta 2-microglobulin, Proc Natl Acad Sci USA, 76, 3651-3655

Louis, N., Evelegh, C., Graham, F. L. (1997) Cloning and sequencing of the cellular-viral junctions from the human adenovirus type 5 transformed 293 cell line, Virology, 233, 423-429

Mayahara H, Ito T, Nagal H, Miyajima H, Tsukuda R, Taketomi S, Mizoguchi J, kato K (1993) In vivo stimulation of endosteal bone formation by basic fibroblast growth factor in rats, Growth Factors, 9, 73-80

Manolagas, S. C. (2000) Birth and death of bone cells: basic regulatory mechanisms and implications for the pathogenesis and treatment of osteoporosis, Endocr. Rev., 21, 115-137

Maruyama K, Sugano S (1994) Oligo-capping: a simple method to replace cap structure of eukaryotic mRNAs with oligoribonucleotides, Gene, 138, 171-174

Myers., W. Technical Report 29, Department of Computer Science, University of Arizona, Tucson, 1991.

Needleman, S. B. & Wunsch, C. D. (1970). A general method applicable to the search for similarities in the amino acid sequence of two proteins. J. Mol. Biol. 48, 443-453.

Neer R. M., Arnaud C. D., Zanchetta J. R., Prince R., Gaich G. A., Reginster J. Y., Hodsman A. B., Eriksen E. F., Ish-Shalom S., Genant H. K., Wang O., Mitlak B. H. (2001) Effect of parathyroid hormone (1-34) on fractures and bone mineral density in postmenopausal women with osteoporosis, N Engl J Med, 344, 1434-41

Olins, G. M., Patton, D. R., Bovy, P. R., Mehta, P. P. (1988) A linear analog of atrial natriuretic peptide (ANP) discriminates guanylate cyclase-coupled ANP receptors from non-coupled receptors, J. Biol. Chem., 263, 10989-10993

Partridge, N. C., Alcorn, D., Michelangeli, V. P., Ryan, G., Martin, T. J. (1983) Morphological and biochemical characterization of four clonal osteogenic sarcoma cell lines of rat origin, Cancer Res., 43, 43084314

Pearson, W. R. & D. J. Lipman., Improved Tools for Biological Sequence Analysis., 1988, Proc. Natl. Acad. Sci., 85, 2444-2448

Ragot, T., et a. (1998), Meth. Cell Biol., 52, 229-260.

Ruchon A. F., Marcinkiewicz M., Siegfried G., Tenenhouse H. S., DesGroseillers L., Crine P., Boileau G. (1998) Pex mRNA is localized in developing mouse osteoblasts and odontoblasts, J Histochem Cytochem, 46, 459-68

Russell, R. G. G, Rogers, M. J. (1999) Bisphosphonates: from the laboratory to the clinic and back again, Bone, 25, 97-106

Smith, T. F. & Waterman, M. S. (1981). Identification of common molecular subsequences. J. Mol. Biol. 147, 195-197.

Tsomides, T. J., Eisen, H. N. (1993) Stoichiometric labeling of peptides by iodination on tyrosyl or histidyl residues, Anal. Biochem., 210, 129-135

Unger, R. H. (2000) Leptin physiology: a seond look, Reg. Pept., 92, 87-95

Wilkinson D G, Nieto M A. (1993) Detection of messenger RNA by in situ hybridization to tissue sections and whole-mounts, Methods Enzymol, 225, 361-73

Yan, W., Sheng, N., Seto, M., Morser, J., Wu, Q. (1999) Corin, a mosaic transmembrane serine protease encoded by a novel cDNA from human heart, J. Biol. Chem., 274, 14926-14935

Yan, W., Wu, F., Morser, J., Wu, Q. (2000) Corin, a transmembrane cardiac serine protease, acts as a pro-atrial natriuretic peptide-converting enzyme, Proc Natl Acad Sci USA, 97, 8525-8529

We claim:

1. An isolated polypeptide comprising SEQ ID NO: 9, wherein the polypeptide regulates at least one of bone cell proliferation, bone cell differentiation and osteoblast activity.

2. An isolated fragment of the polypeptide of claim 1 comprising SEQ ID NO: 20, wherein the fragment regulates at least one of bone cell proliferation, bone cell differentiation and osteoblast activity.

3. The fragment of claim 2 further comprising a label selected from the group consisting of one or more iodinated amino acid residues, one or more biotinylated amino acid residues, and one or more tritiated L-leucines.

4. A pharmaceutical composition comprising the fragment of claim 2 and a pharmaceutically acceptable carrier.

5. An isolated fragment of the polypeptide of claim 1 comprising SEQ ID NO: 46, wherein the fragment regulates at least one of bone cell proliferation, bone cell differentiation and osteoblast activity.

6. The fragment of claim 5 further comprising a label selected from the group consisting of one or more iodinated amino acid residues, one or more biotinylated amino acid residues, and one or more tritiated L-leucines.

7. A pharmaceutical composition comprising the fragment of claim 5 and a pharmaceutically acceptable carrier.

8. An isolated fragment of the polypeptide of claim 1 comprising SEQ ID NO: 21, wherein the fragment regulates at least one of bone cell proliferation, bone cell differentiation and osteoblast activity.

9. The fragment of claim 8 further comprising a label selected from the group consisting of one or more iodinated amino acid residues, one or more biotinylated amino acid residues, and one or more tritiated L-leucines.

10. A pharmaceutical composition comprising the fragment of claim 8 and a pharmaceutically acceptable carrier.

11. An isolated fragment of the polypeptide of claim 1 comprising SEQ ID NO: 47, wherein the fragment regulates at least one of bone cell proliferation, bone cell differentiation and osteoblast activity.

12. The fragment of claim 11 further comprising a label selected from the group consisting of one or more iodinated amino acid residues, one or more biotinylated amino acid residues, and one or more tritiated L-leucines.

13. A pharmaceutical composition comprising the fragment of claim 11 and a pharmaceutically acceptable carrier.

14. An isolated fragment of the polypeptide of claim 1 consisting of SEQ ID NO: 26.

15. The fragment of claim 14 further comprising a label selected from the group consisting of one or more iodinated amino acid residues, one or more biotinylated amino acid residues, and one or more tritiated L-leucines.

16. A pharmaceutical composition comprising the fragment of claim 14 and a pharmaceutically acceptable carrier.

17. An isolated fragment of the polypeptide of claim 1 consisting of SEQ ID NO: 27.

18. The fragment of claim 17 further comprising a label selected from the group consisting of one or more iodinated amino acid residues, one or more biotinylated amino acid residues, and one or more tritiated L-leucines.

19. A pharmaceutical composition comprising the fragment of claim 17 and a pharmaceutically acceptable carrier.

20. An isolated fragment of the polypeptide of claim 1 consisting of SEQ ID NO: 28.

21. The fragment of claim 20 further comprising a label selected from the group consisting of an iodinated tyrosine residue at the fragment's N-terminal, a biotinylated derivative of an amino acid, and a tritiated L-leucine.

22. A pharmaceutical composition comprising the fragment of claim 20 and a pharmaceutically acceptable carrier.

23. The polypeptide of claim 1 further comprising a label selected from the group consisting of one or more iodinated amino acid residues, one or more biotinylated amino acid residues, and one or more tritiated L-leucines.

24. A pharmaceutical composition comprising the polypeptide of claim 1 and a pharmaceutically acceptable carrier.

25. The polypeptide of claim 1, consisting of SEQ ID NO: 9.

26. An isolated fragment of the polypeptide of claim 1, consisting of SEQ ID NO: 20.

27. An isolated fragment of the polypeptide of claim 1, consisting of SEQ ID NO: 21.

28. An isolated fragment of the polypeptide of claim 1, consisting of SEQ ID NO: 46.

29. An isolated fragment of the polypeptide of claim 1, consisting of SEQ ID NO: 47.

30. An isolated polypeptide encoded by the nucleotide sequence of SEQ ID NO: 2.

* * * * *